United States Patent
Salman et al.

(10) Patent No.: US 7,923,467 B2
(45) Date of Patent: Apr. 12, 2011

(54) SUBSTITUTED PYRROLE DERIVATIVES AND THEIR USE AS HMG-CO INHIBITORS

(75) Inventors: Mohammad Salman, Princeton, NJ (US); Jitendra Sattigeri, Haryana (IN); Yatendra Kumar, Haryana (IN); Ram Chander Aryan, Delhi (IN); Vikram Krishna Ramanathan, Haryana (IN); Anita Chugh, Delhi (IN)

(73) Assignee: Ranbaxy Laboratories, Inc., New Delhi, Delhi (IN)

( * ) Notice: Subject to any disclaimer, the term of this patent is extended or adjusted under 35 U.S.C. 154(b) by 1180 days.

(21) Appl. No.: 10/558,859

(22) PCT Filed: May 28, 2004

(86) PCT No.: PCT/IB2004/001761
§ 371 (c)(1),
(2), (4) Date: Aug. 17, 2006

(87) PCT Pub. No.: WO2004/106299
PCT Pub. Date: Dec. 9, 2004

(65) Prior Publication Data
US 2010/0056602 A1    Mar. 4, 2010

Related U.S. Application Data

(63) Continuation-in-part of application No. 10/449,418, filed on May 30, 2003, now abandoned.

(51) Int. Cl.
C07D 405/06    (2006.01)
C07D 207/337    (2006.01)
A61K 31/4025    (2006.01)
A61K 31/40    (2006.01)

(52) U.S. Cl. ......... 514/423; 514/422; 548/517; 548/537
(58) Field of Classification Search .................. 514/423, 514/422; 548/517, 537
See application file for complete search history.

(56) References Cited

U.S. PATENT DOCUMENTS

| | | |
|---|---|---|
| 3,262,977 A | 7/1966 | Harsanyi et al. |
| 3,341,584 A | 9/1967 | Larsen |
| 3,454,635 A | 7/1969 | Weber |
| 3,471,515 A | 10/1969 | Troxler |
| 3,483,221 A | 12/1969 | Wilhelm |
| 3,527,761 A | 9/1970 | Archibald |
| 3,562,257 A | 2/1971 | Kugita |
| 3,576,883 A | 4/1971 | Neuworth |
| 3,642,896 A | 2/1972 | Collin |
| 3,644,353 A | 2/1972 | Lunts et al. |
| 3,649,691 A | 3/1972 | Shavel |
| 3,655,663 A | 4/1972 | Wasson |
| 3,663,570 A | 5/1972 | Sato |
| 3,663,706 A | 5/1972 | Hess et al. |
| 3,669,968 A | 6/1972 | Hess |
| 3,674,836 A | 7/1972 | Creger |
| 3,705,233 A | 12/1972 | Lunts et al. |
| 3,716,583 A | 2/1973 | Nakamura et al. |
| 3,723,446 A | 3/1973 | Scherm et al. |
| 3,773,939 A | 11/1973 | Janssen |
| 3,781,328 A | 12/1973 | Witte |
| 3,850,941 A | 11/1974 | Irikura |
| 3,857,891 A | 12/1974 | Holmes et al. |
| 3,857,952 A | 12/1974 | Wooldridge et al. |
| 3,868,460 A | 2/1975 | Koppe et al. |
| 3,879,554 A | 4/1975 | Temperilli |
| 3,910,924 A | 10/1975 | Tamura et al. |
| 3,912,743 A | 10/1975 | Christensen et al. |
| 3,932,400 A | 1/1976 | Hibino et al. |
| 3,932,645 A | 1/1976 | Meyer et al. |
| 3,934,032 A | 1/1976 | Barrett et al. |
| 3,937,838 A | 2/1976 | Wetterlin et al. |
| 3,948,943 A | 4/1976 | Eberhardt et al. |
| 3,962,238 A | 6/1976 | Mauvernay et al. |
| 3,982,021 A | 9/1976 | Hauck et al. |
| 3,984,413 A | 10/1976 | Metz et al. |
| 3,994,974 A | 11/1976 | Murakami et al. |
| 3,997,666 A | 12/1976 | Witte et al. |
| 3,998,790 A | 12/1976 | Brandstrom et al. |
| 4,011,258 A | 3/1977 | Wetterlin et al. |
| 4,012,444 A | 3/1977 | Lunts et al. |
| 4,032,648 A | 6/1977 | Malen et al. |
| 4,034,009 A | 7/1977 | Zolss et al. |
| 4,051,143 A | 9/1977 | Scherm et al. |
| 4,056,626 A | 11/1977 | Ito et al. |

(Continued)

FOREIGN PATENT DOCUMENTS

CN    1436174    8/2003

(Continued)

OTHER PUBLICATIONS

Patani et al. Chem. Rev. 1996, 96, 3147-3176.* Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Rautio et al. Nature Reviews Drug Discovery 2008, 7, pp. 255-270.*
Wang et al. Drug Delivery: Principles and Applications, 2005 John Wiley & Sons, Inc. Publication, Section 8.3, pp. 136-137.*
Smith, D. A. Current Opinion in Drug Discovery & Development 2007, 10, 550-559.*
Testa, B. Current Opinion in Chemical Biology 2009, 13, pp. 338-344.*

(Continued)

*Primary Examiner* — Joseph R Kosack
*Assistant Examiner* — Matthew P Coughlin
(74) *Attorney, Agent, or Firm* — Sheridan Ross, P.C.

(57) ABSTRACT

The present invention relates to substituted pyrrole derivatives, which can be used as 3-hydroxy-3-methylglutaryl-coenzyme A (HMG-CoA) reductase inhibitors. Compounds disclosed herein can function as cholesterol lowering agents and can be used for the treatment of cholesterol-related diseases and related symptoms. Processes for the preparation of disclosed compounds are provided, as well as pharmaceutical compositions containing the disclosed compounds, and methods of treating cholesterol-related diseases and related symptoms.

23 Claims, No Drawings

U.S. PATENT DOCUMENTS

| | | | |
|---|---|---|---|
| 4,058,552 A | 11/1977 | Mieville | |
| 4,062,950 A | 12/1977 | Frommer et al. | |
| 4,105,776 A | 8/1978 | Ondetti et al. | |
| 4,129,565 A | 12/1978 | Fukushima et al. | |
| 4,154,839 A | 5/1979 | Wehinger et al. | |
| 4,182,767 A | 1/1980 | Murai et al. | |
| 4,188,390 A | 2/1980 | Campbell | |
| 4,217,305 A | 8/1980 | Imai et al. | |
| 4,248,883 A | 2/1981 | Sawayama et al. | |
| 4,252,721 A | 2/1981 | Silvestrini et al. | |
| 4,252,825 A | 2/1981 | Demarne | |
| 4,252,984 A | 2/1981 | Manoury et al. | |
| 4,258,062 A | 3/1981 | Jonas et al. | |
| 4,260,622 A | 4/1981 | Junge et al. | |
| 4,264,611 A | 4/1981 | Berntsson et al. | |
| 4,310,549 A | 1/1982 | Hajos et al. | |
| 4,314,081 A | 2/1982 | Molloy et al. | |
| 4,337,201 A | 6/1982 | Petrillo, Jr. | |
| 4,344,949 A | 8/1982 | Hoefle et al. | |
| 4,410,520 A | 10/1983 | Watthey | |
| 4,425,355 A | 1/1984 | Hoefle et al. | |
| 4,434,176 A | 2/1984 | Troxler et al. | |
| 4,444,779 A | 4/1984 | Kawamatsu et al. | |
| 4,448,964 A | 5/1984 | Muto et al. | |
| 4,466,972 A | 8/1984 | Neumann | |
| 4,470,972 A | 9/1984 | Gold et al. | |
| 4,472,380 A | 9/1984 | Harris et al. | |
| 4,503,067 A | 3/1985 | Wiedemann et al. | |
| 4,508,729 A | 4/1985 | Vincent et al. | |
| 4,522,828 A | 6/1985 | Jeffery et al. | |
| 4,572,909 A | 2/1986 | Campbell et al. | |
| 4,587,258 A | 5/1986 | Gold et al. | |
| 4,598,089 A | 7/1986 | Hadvary et al. | |
| 4,663,325 A | 5/1987 | Ohtaka et al. | |
| 4,672,068 A | 6/1987 | Kutsuma et al. | |
| 4,681,893 A | 7/1987 | Roth | 514/422 |
| 4,687,777 A | 8/1987 | Meguro et al. | |
| 4,699,905 A | 10/1987 | Yanagisawa et al. | |
| 4,701,559 A | 10/1987 | Horii et al. | |
| 4,705,797 A | 11/1987 | Nardi et al. | |
| 4,731,478 A | 3/1988 | Niigata et al. | |
| 4,734,280 A | 3/1988 | Braquet | |
| 4,801,599 A | 1/1989 | Semeraro et al. | |
| 4,822,818 A | 4/1989 | Oka et al. | |
| 4,873,259 A | 10/1989 | Summers, Jr. et al. | |
| 4,879,303 A | 11/1989 | Davison et al. | |
| 4,994,461 A | 2/1991 | Ulrich | |
| 5,002,953 A | 3/1991 | Hindley | |
| 5,049,559 A | 9/1991 | Braquet et al. | |
| 5,128,355 A | 7/1992 | Carini et al. | |
| 5,155,103 A | 10/1992 | Weber et al. | |
| 5,155,120 A | 10/1992 | Lazar et al. | |
| 5,185,351 A | 2/1993 | Finkelstein et al. | |
| 5,273,995 A * | 12/1993 | Roth | 514/422 |
| 5,274,094 A | 12/1993 | Whittaker et al. | |
| 5,344,914 A | 9/1994 | Gibson et al. | |
| 5,349,056 A | 9/1994 | Panayotatos | |
| 5,356,896 A | 10/1994 | Kabadi et al. | |
| 5,385,929 A | 1/1995 | Bjorge et al. | 514/422 |
| 5,399,578 A | 3/1995 | Buhlmayer et al. | |
| 5,422,351 A | 6/1995 | Piwinski et al. | |
| 5,424,286 A | 6/1995 | Eng | |
| 5,466,823 A | 11/1995 | Talley et al. | |
| 5,474,995 A | 12/1995 | Ducharme et al. | |
| 5,491,172 A | 2/1996 | Lee et al. | |
| 5,492,906 A | 2/1996 | Braquet et al. | |
| 5,510,332 A | 4/1996 | Kogan et al. | |
| 5,541,183 A | 7/1996 | Park et al. | |
| 5,552,438 A | 9/1996 | Christensen, IV | |
| 5,559,233 A | 9/1996 | Bernhart et al. | |
| 5,624,941 A | 4/1997 | Barth et al. | |
| 5,633,272 A | 5/1997 | Talley et al. | |
| 5,693,675 A | 12/1997 | Mandeville, III et al. | |
| 5,712,298 A | 1/1998 | Amschler | |
| 5,733,931 A | 3/1998 | Yamada et al. | |
| 5,744,501 A | 4/1998 | Norden | |
| 5,753,653 A | 5/1998 | Bender et al. | |
| 5,767,115 A | 6/1998 | Rosenblum et al. | |
| 5,932,598 A | 8/1999 | Talley et al. | |
| 5,968,982 A | 10/1999 | Voss et al. | |
| 5,985,322 A | 11/1999 | Anderson et al. | |
| 5,990,173 A | 11/1999 | Patoiseau et al. | |
| 5,994,510 A | 11/1999 | Adair et al. | |
| 6,015,557 A | 1/2000 | Tobinick et al. | |
| 6,147,090 A | 11/2000 | DeNinno et al. | |
| 6,197,786 B1 | 3/2001 | DeNinno et al. | |
| 6,268,392 B1 | 7/2001 | Keller et al. | |
| 6,329,336 B1 | 12/2001 | Bridon et al. | |
| 6,329,344 B1 | 12/2001 | Arora et al. | |
| 6,395,751 B1 | 5/2002 | DeNinno et al. | |
| 6,420,417 B1 | 7/2002 | Keller et al. | |
| 6,426,365 B1 | 7/2002 | Shinkai et al. | |
| 6,489,478 B1 | 12/2002 | DeNinno et al. | |
| 6,511,985 B1 | 1/2003 | Ippen et al. | |
| 6,534,088 B2 | 3/2003 | Guivarc'h et al. | |
| 6,569,461 B1 | 5/2003 | Tilyer et al. | |
| 6,586,448 B1 | 7/2003 | DeNinno et al. | |
| 6,590,085 B1 | 7/2003 | Arora et al. | |
| 6,642,268 B2 | 11/2003 | Keller et al. | |
| 6,753,346 B2 | 6/2004 | Shinkai et al. | |
| 6,787,570 B2 | 9/2004 | Sikorski et al. | |
| 6,794,396 B2 | 9/2004 | Lee et al. | |
| 6,803,388 B2 | 10/2004 | Sikorski et al. | |
| 6,884,226 B2 | 4/2005 | Pereira | |
| 6,992,194 B2 | 1/2006 | Lidor-Hadas et al. | |
| 7,056,936 B2 | 6/2006 | Kilian et al. | |
| 7,361,772 B2 | 4/2008 | Mathew et al. | |
| 2002/0052312 A1 | 5/2002 | Reiss et al. | |
| 2002/0183378 A1 | 12/2002 | Aronhime et al. | |
| 2003/0153617 A1 | 8/2003 | Dalen et al. | |
| 2004/0029962 A1 | 2/2004 | Chen et al. | |
| 2004/0053842 A1 | 3/2004 | Nguyen et al. | |
| 2004/0097555 A1 | 5/2004 | Ohkawa et al. | |
| 2004/0102511 A1 * | 5/2004 | Sattigeri et al. | 514/422 |
| 2004/0132771 A1 | 7/2004 | Babcock et al. | |
| 2005/0032878 A1 | 2/2005 | Deboeck et al. | |
| 2005/0063911 A1 | 3/2005 | Nilsson et al. | |
| 2005/0187204 A1 | 8/2005 | Kondo et al. | |
| 2007/0238716 A1 | 10/2007 | Murthy et al. | |
| 2007/0259874 A1 | 11/2007 | Palle et al. | |
| 2008/0153896 A1 | 6/2008 | Yadav et al. | |
| 2008/0248035 A1 | 10/2008 | Sattigeri et al. | |
| 2008/0287690 A1 | 11/2008 | Kaul et al. | |
| 2009/0118520 A1 | 5/2009 | Sattigeri et al. | |

FOREIGN PATENT DOCUMENTS

| | | |
|---|---|---|
| EP | 0 247 633 | 12/1987 |
| EP | 0409281 | 1/1991 |
| EP | 0419049 | 3/1991 |
| EP | 0542355 | 5/1993 |
| EP | 0542356 | 5/1993 |
| EP | 0606646 | 7/1994 |
| EP | 0651739 | 5/1995 |
| EP | 0 680 963 | 11/1995 |
| EP | 0753298 | 1/1997 |
| EP | 0818197 | 1/1998 |
| EP | 0818448 | 1/1998 |
| EP | 0842943 | 5/1998 |
| EP | 0903353 | 3/1999 |
| EP | 0905139 | 3/1999 |
| EP | 0918059 | 5/1999 |
| EP | 1488808 | 12/2004 |
| EP | 1510208 | 3/2005 |
| EP | 1523316 | 4/2005 |
| JP | 2003-104883 | 4/2003 |
| RU | 2005102839 A | 7/2006 |
| UA | 72 290 C2 | 2/2005 |
| WO | WO 95/15973 | 6/1995 |
| WO | WO 95/28926 | 11/1995 |
| WO | WO 96/01644 | 1/1996 |
| WO | WO 96/06108 | 2/1996 |
| WO | WO 96/20216 | 7/1996 |
| WO | WO 96/22966 | 8/1996 |
| WO | WO 96/31206 | 10/1996 |
| WO | WO 96/40641 | 12/1996 |
| WO | WO 96/40781 | 12/1996 |
| WO | WO 97/02289 | 1/1997 |

| | | |
|---|---|---|
| WO | WO 97/03094 | 1/1997 |
| WO | 97/16184 | 5/1997 |
| WO | WO 97/22619 | 6/1997 |
| WO | WO 98/19998 | 5/1998 |
| WO | WO 98/27098 | 6/1998 |
| WO | WO 98/47892 | 10/1998 |
| WO | WO 98/53814 | 12/1998 |
| WO | WO 98/53817 | 12/1998 |
| WO | WO 98/53818 | 12/1998 |
| WO | WO 98/54207 | 12/1998 |
| WO | WO 99/11259 | 3/1999 |
| WO | 99/20110 | 4/1999 |
| WO | WO 99/23063 | 5/1999 |
| WO | WO 99/24398 | 5/1999 |
| WO | WO 99/35163 | 7/1999 |
| WO | WO 99/36393 | 7/1999 |
| WO | WO 99/37605 | 7/1999 |
| WO | WO 99/37618 | 7/1999 |
| WO | 99/47138 | 9/1999 |
| WO | WO 99/43642 | 9/1999 |
| WO | WO 99/47547 | 9/1999 |
| WO | WO 99/54321 | 10/1999 |
| WO | 99/58505 | 11/1999 |
| WO | WO 99/58902 | 11/1999 |
| WO | WO 99/61465 | 12/1999 |
| WO | WO 99/67230 | 12/1999 |
| WO | WO 00/00477 | 1/2000 |
| WO | WO 00/01690 | 1/2000 |
| WO | WO 00/05223 | 2/2000 |
| WO | WO 00/05224 | 2/2000 |
| WO | WO 00/15612 | 3/2000 |
| WO | WO 00/18759 | 4/2000 |
| WO | WO 00/18760 | 4/2000 |
| WO | WO 00/35425 | 6/2000 |
| WO | WO 00/43384 | 7/2000 |
| WO | WO 01/13953 | 3/2001 |
| WO | 01/37831 | 5/2001 |
| WO | WO 01/32127 | 5/2001 |
| WO | WO 01/42246 | 6/2001 |
| WO | WO 01/53257 | 7/2001 |
| WO | WO 01/93860 | 12/2001 |
| WO | WO 01/96311 | 12/2001 |
| WO | WO 02/13797 | 2/2002 |
| WO | WO 02/43732 | 6/2002 |
| WO | WO 02/051804 | 7/2002 |
| WO | WO 02/096422 | 12/2002 |
| WO | 03/007993 | 1/2003 |
| WO | WO 03/013607 | 2/2003 |
| WO | WO 03/013608 | 2/2003 |
| WO | WO 03/066063 | 8/2003 |
| WO | 03/077896 | 9/2003 |
| WO | WO 03/080070 | 10/2003 |
| WO | WO 03/088962 | 10/2003 |
| WO | 03/094923 | 11/2003 |
| WO | WO 2004/004777 | 1/2004 |
| WO | WO 2004/004778 | 1/2004 |
| WO | WO 2004/014896 | 2/2004 |
| WO | WO 2004/019985 | 3/2004 |
| WO | 2004/028456 | 4/2004 |
| WO | WO 2004/039373 | 5/2004 |
| WO | 2004/056395 | 7/2004 |
| WO | 2004/062557 | 7/2004 |
| WO | WO 2004/056359 | 7/2004 |
| WO | WO 2004/067006 | 8/2004 |
| WO | WO 2004/098583 | 11/2004 |
| WO | 2004/106299 | 12/2004 |
| WO | 2005/014539 | 2/2005 |
| WO | WO 2005/009340 | 2/2005 |
| WO | WO 2005/018626 | 3/2005 |
| WO | WO 2005/021515 | 3/2005 |
| WO | WO 2005/026163 | 3/2005 |
| WO | WO 2005/034908 | 4/2005 |
| WO | WO 2005/041864 | 5/2005 |
| WO | WO 2005/051931 | 6/2005 |
| WO | WO 2005/056536 | 6/2005 |
| WO | WO 2005/058813 | 6/2005 |
| WO | WO 2005/058898 | 6/2005 |
| WO | WO 2005/100318 | 10/2005 |
| WO | WO 2005/100331 | 10/2005 |
| WO | WO 2006/085212 | 8/2006 |
| WO | WO 2006/117743 | 11/2006 |
| WO | WO 2007/054789 | 5/2007 |
| WO | WO 2007/054790 | 5/2007 |
| WO | WO 2007/054896 | 5/2007 |

OTHER PUBLICATIONS

Fura, A. DDT, 2006, 11, pp. 133-142.*
Anari et al. DDT, 2005, 10, pp. 711-717.*
Nedderman, A. N. R. Biopharm. Drug Dispos. 2009, 30, pp. 152-162.*
Examination Report for New Zealand Patent Application No. 577031, dated Sep. 25, 2009.
Examination Report for Colombian Patent Application No. 05-121.080, dated Oct. 28, 2009.
Examination Report for European Patent Application No. 04735296.8, mailed Nov. 13, 2009.
International Search Report for International (PCT) Patent Application No. PCT/IB2006/003152, mailed Apr. 3, 2007.
Written Opinion for International (PCT) Patent Application No. PCT/IB2006/003152, mailed Apr. 3, 2007.
International Search Report for International (PCT) Patent Application No. PCT/IB2004/001761, mailed Jan. 3, 2005.
Written Opinion for International (PCT) Patent Application No. PCT/IB2004/001761, mailed Jan. 3, 2005.
International Preiliminary Report on Patentability for International (PCT) Patent Application No. PCT/IB2004/001761, mailed Dec. 15, 2005.
Search Report for Georgian Patent Application No. AP 2004 009124, dated Nov. 7, 2006.
Written Opinion for Singapore Patent Application No. 200507449-7, dated Sep. 6, 2006.
Second Written Opinion for Singapore Patent Application No. 200507449-7, dated Mar. 3, 2007.
First Official Letter for Eurasian Patent Application No. 200501881.
Antibacterial & Antifungal Drug Discovery & Development Summit, Strategic Research Institute, Jun. 28-29, 2001, Amsterdam, The Netherlands.
Bundgaard, H., 1985. *Design of Prodrugs*. New York:Elsevier.
Heller et al., "Solubilization and Partial Purification of Hepatic 3-Hydroxy-3-Methylglutaryl Coenzyme A Reductase," *Biochemical and Biophysical Research Communications*, 50(3):859-865 (1973).
Bedford et al, "Nonquaternary Cholinesterase Reactivators. 3 . 3(5)-Substituted 1,2,4-Oxadiazol-5(3)-aldoximes and 1,2,4-Oxidiazole-5(3)-thiocarbohydroximates as Reactivators of Organophosphonate-Inhibited Eel and Human Acetylcholinesterase in Vitro", *Journal of Medicinal Chemistry*, 29(11):2174-2183 (1986).
Renodon-Corniere et al, "N-Aryl N'Hydroxyguanidines, A New Class of NO-Donors after Selective Oxidation by Nitric Oxide Synthases: Structure-Activity Relationship," *Journal of Medicinal Chemistry*, 45(4):944-954 (2002).
Meyer et al, "Annulation of α-Formyl α,β-Unsaturated Ketones by a Michael Addition-Cyclization Sequence. A Versatile Synthesis of Alicyclic Six-Membered Rings", *Journal of Organic Chemistry*, 50(4):438-447 (1985).
Kubo and Strott, "Differential Activity of 3-Hydroxy-3-Methylglutaryl Coenzyme A Reductase in Zones of the Adrenal Cortex," *Endocrinology*, 120(1):214-221 (1987).
Sun et al, "A general synthesis of dioxolenone prodrug moieties", *Tetrahedron Letters*, 43:1161-1164 (2002).
"Prevent" definition from dictionary.com, accessed Nov. 28, 2007.
Allain et al., Clin. Chem., 20:470 (1974).
Baumann et al., "The Convergent Synthesis of CI-981, an Optically Active, Highly Potent, Tissue Selective Inhibitor of HMG-COA Reductase", Tetrahedron Letters, Elsevier, vol. 33, No. 17, Apr. 21, 1992, pp. 2283-2284.
Carr et al., "Enzymatic Determination of Triglyceride, Free Cholesterol, and Total Cholesterol in Tissue Lipid Extracts", Clin. Biochem., 26:39-42 (1993).
Cui et al., J. Biol. Chem., 278:10214-10220 (2003).
Dolinsky et al., Biochem. J., 378:967-974 (2004).
Frederikson et al., J. Lipid Res., 45:592-601 (2004).
Friedewald et al., Clin. Chem., 18:6, pp. 499-502 (1972).

Frings et al., Clin. Chem., 18(7), pp. 673-4 (1972).
Fujino et al., "Metabolic properties of the acid and lactone froms of HMG-CoA reductasse inhibitors", Xenobiotica, Nov./Dec. 2004, vol. 34, No. 11/12, pp. 961-971.
Ruys et al., "The Estimation of Serum Triglycerides by Nephelometry: A Simple Method for the Estimation of Serum Triglycerides Suitable for the Small Laboratory", Med. J. Aust., 22(1):385-387 (1975).
Harwood et al., J. Lipid Res., 34:377-395 (1993).
Niculescu-Duvaz D et al., "Self-Immolative Nitrogen Mustard Profdrugs for Suicide Gene Therapy", J. Med. Chem. 41(26):5297-5309 (1998).
Lorenzen et al., Mol. Pharmacol., 59:349-357 (2001).
Nakanishi, K., "Terpene trilactones from Gingko bioloba: From ancient times to the 21st century", Bioorg. Med. Chem., 13:4987-5000 (2005).
Rifai et al., Clin. Chem., 32(6):957-961 (1986).
Rinaldi-Carmona et al., "Biochemical and Pharmacological Characterisation of SR141716A, the first potent and selective brain cannabinoid receptor antagonist", Life Sci., 56:1941-1947 (1995).
Rodriguez-Sureda et al., "A Procedure for measuring triacylglyceride and cholesterol content using a small amount of tissue", Anal. Biochem., 343:277-282 (2005).
Sampson et al., Clin. Chem., 47(3):532-539 (2001).
Shefer et al., J. Lipid Res., 22:532-536 (1981).
Karimi et al., "Lithium triflate (LiOTf) catalyzed efficient and chemoselective tetrahydropyranylation of alcohols and phenols under mild and neutral reaction conditions", Tetrahedron Lett., 43(30):5353 (2002).
Wilson et al., "Estimation of VLDL cholesterol in hyperlipidemia", Clin. Chim. Acta., Oct. 15; 1513:285-291 (1985).
Zhang et al., "Niacin mediates lipolysis in adipose tissue through its G-protein coupled receptor HM74A", Biochem and Biophys. Res. Commun., 334:729-732 (2005).
U.S. Appl. No. 60/498,947, filed Aug. 29, 2003, entitled "Isoxazoline derivatives as inhibitors or phophodiesterase type-IV".
Translation of First Office Action for Chinese Patent Application No. 200480018099.2, mailed Jun. 29, 2007.
Decision on Rejection (including translation) for Chinese Patent Application No. 200480018099.2, mailed Mar. 28, 2008.
Examination Report for European Patent Application No. 04735296.8, mailed Jun. 18, 2007.
Examination Report for European Patent Application No. 04735296.8, mailed Mar. 12, 2008.
Substantive Examination Examiner's Report for Malaysian Patent Application No. PI 2004 2094, dated Jul. 10, 2008.
Examination Report for New Zealand Patent Application No. 543741, dated Jan. 24, 2008.
Examination Report for New Zealand Patent Application No. 577031 dated May 20, 2009.

Official Action for Phillipines Patent Application No. 1-2005-502127, mailed Jan. 30, 2009.
Official Action for Papua New Guinea Patent Application No. PG/P/05/00043, dated Jan. 5, 2009.
Invitation to Pay Additional Fees for International (PCT) Patent Application No. PCT/IB2004/001761, mailed Oct. 4, 2004.
Notice on Reexamination for Chinese Patent Application No. 200480018099.2, mailed May 13, 2009.
Examination Report for New Zealand Patent Application No. 577031 dated Sep. 18, 2009.
U.S. Appl. No. 12/092,813, filed May 6, 2008, Sattigeri et al.
Baumann et al., "The Convergent Synthesis of CI-981, an Optically Active, Highly Potent, Tissue Selective Inhibitor of HMG-COA Reductase", Tetrahedron Letters, Elsevier, vol. 33, No. 17, Apr. 21, 1992, pp. 2283-2284.
U.S. Appl. No. 60/498,947, filed Aug. 29, 2003, entitled "Isoxazoline derivatives as inhibitors or phophodiesterase type-IV".
Anderson, "Chapter 10: Work-up," in Practical Process Research & Development, 2000, pp. 203-221.
Athyros et al., "Atorvastatin and Micronized Fenofibrate Alone and in Combination in Type 2 Diabetes with Combined Hyperlipidemia," Diabetes Care, 2002, vol. 25, pp. 1198-1202.
Bravo, et al., "Prevalence of Potentially Severe Drug-Drug Interactions in Ambulatory Patients with Dyslipidaemia Receiving HMG-CoA Reductase Inhibitor Therapy," Drug Safety 2005: 28(3):263-275.
Byrn et al., "Chapter 11: Hydrates and Solvates," Solid-State Chemistry of Drugs (2nd Ed.), 1999, pp. 233-247.
Morissette et al., "High-throughput crystallization: polymorphs, salts, co-crystals and solvates of pharmaceutical solids," Adv. Drug Delivery Rev. 2004, vol. 56, pp. 275-300.
Wilke, et al., "Relative impact of CYP3A genotype and concomitant medication on the severity of atorvastatin-induced muscle damage," Pharmacogenetics and Genomics 2005, 15(6):415-421.
Examiner's First Report on Australian Patent Application No. 2004242777, dated Feb. 11, 2010.
Translation of First Office Action for Japanese Patent Application No. 2006-530701, dispatched Jul. 13, 2010.
Office Action (including translation) for Cuban Patent Application No. 2005-0240, dated Apr. 14, 2010.
Office Action for Israel Patent Application No. 172257, No Date, 2010.
Brittain (Polymorphism in Pharmaceutical Solids, vol. 95, 1999, Taylor & Francis, Harry G. Brittain (Ed.), 427 pp.).
Byrn et al., "Pharmaceutical Solids: A Strategic Approach to Regulatory Considerations," Pharmaceutical Research, 1995, vol. 12, No. 7, pp. 945-954.

* cited by examiner

SUBSTITUTED PYRROLE DERIVATIVES AND THEIR USE AS HMG-CO INHIBITORS

CROSS-REFERENCE TO RELATED APPLICATIONS

This application is the 35 U.S.C. 371 National Stage Application of PCT/IB04/01761, filed May 28, 2004, which is a continuation-in-part of U.S. patent application Ser. No. 10/449,418, filed May 30, 2003, now abandoned.

FIELD OF THE INVENTION

The present invention relates to substituted pyrrole derivatives, which can be used as 3-hydroxy-3-methylglutaryl-coenzyme A (HMG-CoA) reductase inhibitors.

Compounds disclosed herein can function as cholesterol lowering agents and can be used for the treatment of cholesterol-related diseases and related symptoms. Processes for the preparation of disclosed compounds are provided, as well as pharmaceutical compositions containing the disclosed compounds, and methods of treating cholesterol-related diseases and related symptoms.

BACKGROUND OF THE INVENTION

Cardiovascular disease and its associated maladies, dysfunctions and complications are a principal cause of disability and the chief cause of death. One specific factor significantly contributing to this pathophysiologic process is atherosclerosis, which has been generally recognized as the leading health care problem both with respect to mortality and health care costs.

Atherosclerosis is characterized by the deposition of fatty substances, primarily cholesterol, resulting in plaque formation on the inner surface of the arterial wall and degenerative change to the arteries.

It is now well established that cardiovascular disorders including myocardial infarction, coronary heart disease, hypertension and hypotension, cerebrovascular disorders including stroke, cerebral thrombosis and memory loss due to stroke; peripheral vascular disease and intestinal infarction are caused by blockage of arteries and arterioles by atherosclerotic plaque. Atherosclerotic plaque formation is multifactorial in its production. Hypercholesterolemia, especially elevated levels of low-density lipoprotein cholesterol (LDL), is an important risk factor for atherosclerosis and arteriosclerosis and associated diseases.

The HMG-CoA reductase inhibitors (statins) have been used in reducing blood levels of LDL cholesterol. Cholesterol is produced via the mevalonic acid pathway. Reducing the formation of mevalonic acid, a precursor to cholesterol, leads to a corresponding decrease in hepatic cholesterol biosynthesis with a reduction in the cellular pool of cholesterol.

U.S. Pat. No. 4,681,893 assigned to Warner-Lambert, discloses certain trans-6-[2-(3-, or 4-carboxamido-substituted pyrrole-1-yl)alkyl]-4-hydroxypyran-2-ones and the corresponding ring-opened hydroxy acids derived therefrom, including trans(±)-5-(4-fluorophenyl)-2-(1-methylethyl)-N,4-diphenyl-1-[2-tetrahydrohydroxy-6-oxo-2H-pyran-2-yl)ethyl]-1H-pyrrole-3-carboxamide, which are inhibitors of 3-hydroxy-3-methylglutaryl-coenzyme A reductase (HMG-CoA), an important coenzyme catalyzing the intracellular synthesis of cholesterol.

U.S. Pat. No. 5,273,995 assigned to Warner Lambert, relates to the optically pure (R,R) form of the ring-opened acid of trans-5-(4-fluorophenyl)-2-(1-methylethyl-N,4-diphenyl-1-[2-tetrahydro-4-hydroxy-6-oxo-2H-pyran-2-yl)ethyl]-1H-pyrrole-3-carboxamide that is [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid, pharmaceutically acceptable salts thereof, specifically its calcium salt (Atorvastatin, Lipitor®), which is currently being used for the treatment of hypercholesterolemia.

U.S. Pat. No. 5,385,929 discloses certain phenyl hydroxy derivatives of the compounds disclosed in U.S. Pat. No. 5,273,995, and that such phenyl hydroxy derivatives are also active as the inhibitors of the biosynthesis of cholesterol.

SUMMARY OF THE INVENTION

The present invention relates to substituted pyrrole derivatives, which can be used as 3-hydroxy-3-methylglutaryl-coenzyme A (HMG-CoA) reductase inhibitors, and processes for the synthesis of these compounds. These compounds show utility in inhibiting HMG-CoA reductase, among the key rate limiting steps in the biosynthetic pathway of cholesterol formation. Therefore, these compounds hold promise for the treatment of hypercholesterolemia and hyperlipidemia Pharmaceutically acceptable salts, pharmaceutically acceptable solvates, tautomers, racemates, polymorphs, pure enantiomers, diastereoisomers, metabolites, prodrugs or N-oxides of these compounds having the same type of activity are also provided.

Pharmaceutical composition containing the compounds, and which may also contain pharmaceutically acceptable carriers or diluents, which can be used for the treatment of cholesterol-related disease or related symptoms thereof are also provided.

Other aspects will be set forth in the accompanying description which follows and in the part will be apparent from the description or may be learnt by the practice of the invention.

In accordance with another aspect, there is provided a method for treating a mammal suffering from cholesterol related disease, diabetes and related disease, cerebrovascular disease or cardiovascular disease, comprising administering to a mammal a therapeutically effective amount of compounds disclosed herein.

The compounds of the present invention can be used for treating arteriosclerosis, atherosclerosis, hypercholesterolemia, hyperlipidemia, hyperlipoproteinemia, hypertriglyceridemia, hypertension, stroke, ischemia, endothelium dysfunction, peripheral vascular disease, peripheral arterial disease, coronary heart disease, myocardial infarction, cerebral infarction, myocardial microvascular disease, dementia, Alzheimer's disease, osteoporosis and/or osteopenia, angina or resterosis.

In accordance with one aspect, there is provided a compound having the structure of Formula I,

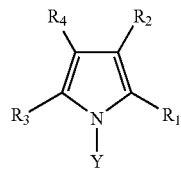

Formula I its pharmaceutically acceptable salts, pharmaceutically acceptable solvates, prodrugs, metabolites, polymorphs, tautomers, racemates, pure enantiomers, diastereoisomers or N-oxides wherein $Y =$ 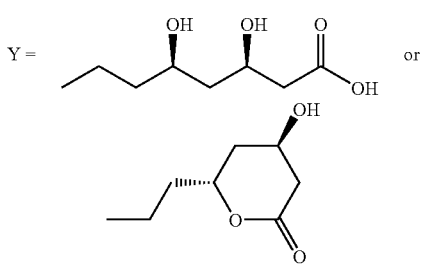 or $R_1$ can be $C_1$-$C_6$, $C_3$-$C_6$, or optionally substituted phenyl (wherein up to three substituents are independently selected from halogens, $C_1$-$C_6$ alkyl, cyano, or $C_1$-$C_3$ perfluoroalkyl);
$R_2$ can be optionally substituted phenyl (wherein up to three substituents are independently selected from cyano, acetyl, or optionally substituted amino, wherein up to two amino substituents are independently selected from $C_1$-$C_6$ alkyl, $C_3$-$C_6$ cycloalkyl, acetyl, or sulfonamide);
$R_3$ can be optionally substituted $C_1$-$C_6$ alkyl or $C_3$-$C_6$ cycloalkyl (wherein substituents are independently selected from halogens, hydroxyl, $C_1$-$C_3$ alkoxy and protected hydroxyl);
$R_3$ can also be —$NR_8R_9$, wherein $R_8$ and $R_9$ are optionally substituted $C_1$-$C_6$ alkyl (wherein the optional substituent(s) is/are selected from halogens, hydroxy, $C_1$-$C_3$ alkoxy and protected hydroxyl);
$R_4$ can be

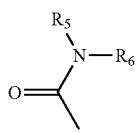

wherein $R_5$ and $R_6$ are independently hydrogen, $C_1$-$C_6$ alkyl or $C_3$-$C_6$ cycloalkyl, optionally substituted aryl or aralkyl, wherein the substituents are selected from halogens, cyano, optionally substituted $C_1$-$C_6$ alkyl (wherein up to two substituents are independently selected from hydroxyl, protected hydroxyl, and halogen(s)), optionally substituted amino (wherein up to two substituents are independently selected from $SO_2R_7$, $COR_7$, or $CONHR_7$, wherein $R_7$ is $C_1$-$C_6$ alkyl or aryl), or acetyl, trifluoromethyl, or $C_1$-$C_6$ alkoxycarbonyl, or $R_5$ and $R_6$ together form a 5-7 membered ring with one or more optional heteroatoms wherein the hetero atom(s) are independently selected from nitrogen, oxygen and sulfur, or $R_4$ can be an optionally substituted mono-, bi- or tricyclic heterocycle having one or more hetero atom(s) wherein said hereto atom(s) is/are independently selected from oxygen, nitrogen and sulfur, and the optional substituents are independently selected from halogens, hydroxy, protected hydroxyl, $C_1$-$C_3$ alkoxy, cyano, $C_1$-$C_3$ perfluoroalkyl, $C_1$-$C_6$ alkyl or $C_3$-$C_6$ cycloalkyl, aryl or optionally substituted aralkyl wherein the substituents are independently selected from halogens, hydroxy, protected hydroxyl, $C_1$-$C_3$ alkoxy, cyano, or $C_1$-$C_3$ perfluoroalkyl,
and the pharmaceutically acceptable salts, tautomers, racemates, pure enantiomers or diastereoisomers, and solvates of the compounds of Formula I,
with the proviso that $R_2$ is phenyl only when (1) $R_5$ or $R_6$ is $C_3$-$C_6$ cycloalkyl or phenyl substituted with acetyl, alkyl, cycloalkyl, hydroxyalkyl, alkylsulfonamido, acetamido or (2) when $R_5$ and $R_6$ together form a 5-7 membered ring with or without one or more heteroatoms wherein the hetero atom(s) are selected from nitrogen, oxygen and sulfur or (3) when $R_5$ or $R_6$ is aralkyl optionally substituted with halogens, cyano, $C_1$-$C_6$ alkyl, $C_1$-$C_6$ halogenated alkyl or (4) when $R_4$ is optionally substituted mono-, bi- or tricyclic heterocycle having one or more hetero atom(s) (wherein the optional substituents are independently selected from halogens, hydroxy, protected hydroxyl, $C_1$-$C_3$ alkoxy, cyano, perfluoroalkyl of one to three carbon atoms, $C_1$-$C_6$ alkyl, $C_3$-$C_6$ cycloalkyl, aryl, or optionally substituted aralkyl (wherein the aralkyl substituents are independently selected from halogens, hydroxy, protected hydroxyl, $C_1$-$C_3$ alkoxy, cyano, or $C_1$-$C_3$ perfluoroalkyl)).

In accordance with another aspect, there are provided compounds having the structure of Formula Ib, Formula Ib

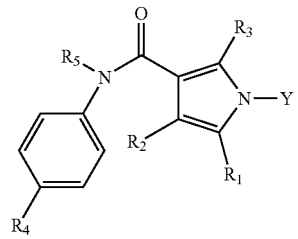

their pharmaceutically acceptable salts, pharmaceutically acceptable solvates, tautomers, racemates, polymorphs, pure enantiomers, diastereoisomers, metabolites, prodrugs or N-oxides wherein $Y =$ 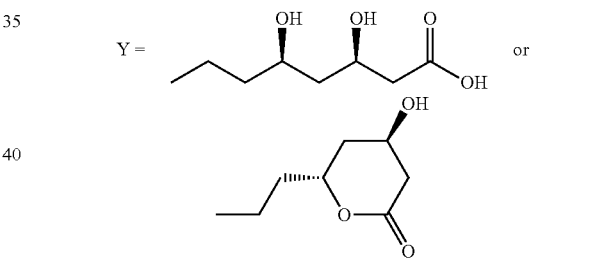 or $R_1$ can be $C_1$-$C_6$ alkyl, $C_3$-$C_6$ cycloalkyl, or optionally substituted phenyl (wherein the substituent(s) is/are selected from halogens, $C_1$-$C_6$ alkyl, cyano and $C_1$-$C_3$ perfluoroalkyl);
$R_2$ can be optionally substituted phenyl (wherein the substituent(s) is/are selected from cyano, acetyl and optionally substituted amino);
$R_3$ can be optionally substituted $C_1$-$C_6$ alkyl or $C_3$-$C_6$ cycloalkyl (wherein the substituent(s) is/are selected from halogens, hydroxyl, $C_1$-$C_3$ alkoxy, and protected hydroxyl);
$R_3$ can also be —$NR_6R_7$ wherein $R_6$ and $R_7$ are optionally substituted $C_1$-$C_6$ alkyl (wherein the optional substituent(s) is/are selected from halogens, hydroxyl, $C_1$-$C_3$ alkoxy, and protected hydroxyl);
$R_4$ can be acetyl, $C_1$-$C_2$ alkoxycarbonyl, optionally substituted $C_1$-$C_6$ alkyl (wherein the substituent is hydroxy or protected hydroxyl), $NHR_8$ [wherein $R_8$ is selected from alkyl, aralkyl, $SO_2R_9$, $COR_9$ or $CONHR_9$, $CSNHR_9$ (wherein $R_9$ is $C_1$-$C_6$ alkyl, aryl or aralkyl)]; $R_4$ can also be —$COR_{10}$ (wherein $R_{10}$ is selected from hydroxyl and —$NR_{11}R_{12}$ (wherein $R_{11}$ and $R_{12}$ are independently selected from hydrogen, alkyl, aryl, $C_3$-$C_7$ cycloalkyl, heterocyclyl, aralkyl and $R_{11}$ and $R_{12}$ together form 5-7 membered ring with one or more optional heteroatom(s) wherein the heteroatom(s) is/are independently selected from nitrogen, oxygen and sulphur);
$R_5$ can be hydrogen, $C_1$-$C_6$ alkyl or $C_3$-$C_6$ cycloalkyl, optionally substituted aryl or aralkyl [wherein the substituents are selected from halogens, cyano, optionally substituted $C_1$-$C_6$ alkyl (wherein the substituents are independently selected from hydroxyl, protected hydroxyl, and halogen(s)], optionally substituted amino, acetyl, trifluoromethyl and $C_1$-$C_6$ alkoxycarbonyl.

In one particular embodiment, there are provided compounds of Formula Ib,

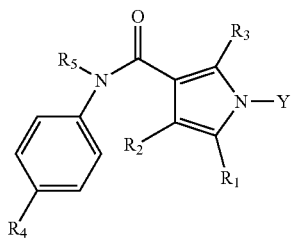

Formula Ib their pharmaceutically acceptable salts, pharmaceutically acceptable solvates, tautomers, racemates, polymorphs, pure enantiomers, diastereoisomers, metabolites, prodrugs or N-oxides wherein

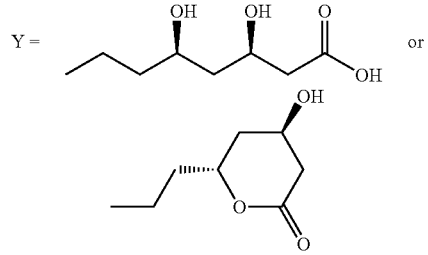

$R_1$, $R_2$, $R_3$ and $R_5$ are as defined earlier;
$R_4$ can be NHR$_8$ [wherein R$_8$ is selected from aralkyl, CONHR$_9$ (wherein R$_9$ is aralkyl); CSNHR$_9$ (wherein R$_9$ is $C_1$-$C_6$ alkyl, aryl or aralkyl)]; —COR$_{10}$ (wherein R$_{10}$ is selected from hydroxyl and —NR$_{11}$R$_{12}$ (wherein R$_{11}$ and R$_{12}$ are independently selected from hydrogen, alkyl, aryl, $C_3$-$C_7$ cycloalkyl, aralkyl and R$_{11}$ and R$_{12}$ together form 5-7 membered ring with one or more optional heteroatom(s) wherein the heteroatom(s) is/are independently selected from nitrogen, oxygen and sulphur);

In yet another particular embodiment, there are provided compounds of Formula Ib,

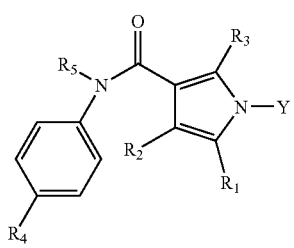

Formula Ib their pharmaceutically acceptable salts, pharmaceutically acceptable solvates, tautomers, racemates, polymorphs, pure enantiomers, diastereoisomers, metabolites, prodrugs or N-oxides wherein

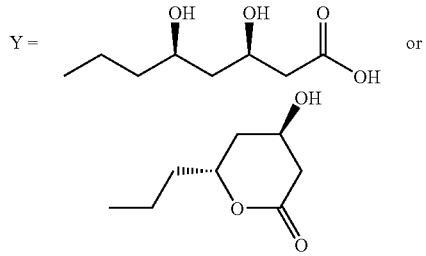

$R_1$, $R_2$, $R_3$ and $R_5$ can be 4-fluorophenyl, phenyl, isopropyl and hydrogen, respectively;
$R_4$ can be $C_1$-$C_2$ alkoxycarbonyl, optionally substituted $C_1$-$C_6$ alkyl (wherein the substituent is hydroxy or protected hydroxyl), NHR$_8$ [wherein R$_8$ is selected from SO$_2$R$_9$, COR$_9$ or CONHR$_9$ (wherein R$_9$ is methyl or phenyl)]

In accordance with further aspect, there are provided intermediates having the structure of Formula XIX,

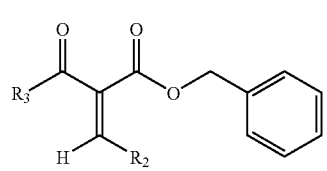

Formula XIX wherein
$R_2$ can be optionally substituted phenyl (wherein the substituent(s) is/are selected from cyano, acetyl and optionally substituted amino;
$R_3$ can be optionally substituted $C_1$-$C_6$ alkyl or $C_3$-$C_6$ cycloalkyl (wherein the substituent(s) is/are selected from halogens, hydroxyl, $C_1$-$C_3$ alkoxy, and protected hydroxyl);
$R_3$ can also be —NR$_6$R$_7$ wherein R$_6$ and R$_7$ are optionally substituted $C_1$-$C_6$ alkyl (wherein the optional substituent(s) is/are selected from halogens, hydroxyl, $C_1$-$C_3$ alkoxy, and protected hydroxyl).

In accordance with third aspect, there are provided intermediates having the structure of Formula XX,

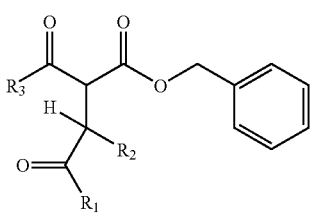

Formula XX wherein
$R_1$ can be $C_1$-$C_6$ alkyl, $C_3$-$C_6$ cycloalkyl, or optionally substituted phenyl (wherein the substituent(s) is/are selected from halogens, $C_1$-$C_6$ alkyl, cyano and $C_1$-$C_3$ perfluoroalkyl);
$R_2$ can be optionally substituted phenyl (wherein the substituent(s) is/are selected from cyano, acetyl and optionally substituted amino;

$R_3$ can be optionally substituted $C_1$-$C_6$ alkyl or $C_3$-$C_6$ cycloalkyl (wherein the substituent(s) is/are selected from halogens, hydroxyl, $C_1$-$C_3$ alkoxy, and protected hydroxyl); $R_3$ can also be —$NR_6R_7$ wherein $R_6$ and $R_7$ are optionally substituted $C_1$-$C_6$ alkyl (wherein the optional substituent(s) is/are selected from halogens, hydroxyl, $C_1$-$C_3$ alkoxy, and protected hydroxyl).

In accordance with fourth aspect, there are provided intermediates having the structure of Formula XXI, Formula XXI

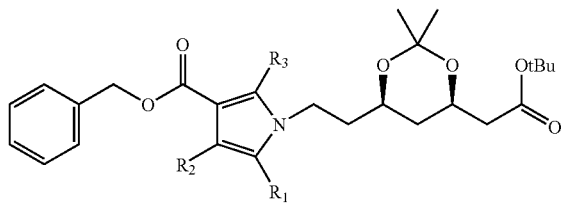

wherein
$R_1$ can be $C_1$-$C_6$ alkyl, $C_3$-$C_6$ cycloalkyl, or optionally substituted phenyl (wherein the substituent(s) is/are selected from halogens, $C_1$-$C_6$ alkyl, cyano and $C_1$-$C_3$ perfluoroalkyl);
$R_2$ can be optionally substituted phenyl (wherein the substituent(s) is/are selected from cyano, acetyl and optionally substituted amino;
$R_3$ can be optionally substituted $C_1$-$C_6$ alkyl or $C_3$-$C_6$ cycloalkyl (wherein the substituent(s) is/are selected from halogens, hydroxyl, $C_1$-$C_3$ alkoxy, and protected hydroxyl); $R_3$ can also be —$NR_6R_7$ wherein $R_6$ and $R_7$ are optionally substituted $C_1$-$C_6$ alkyl (wherein the optional substituent(s) is/are selected from halogens, hydroxyl, $C_1$-$C_3$ alkoxy, and protected hydroxyl).
In accordance with fifth aspect, there are provided intermediates having the structure of Formula XXII, Formula XXII

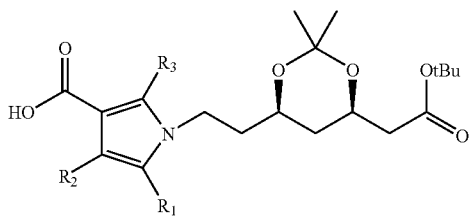

wherein
$R_1$ can be $C_1$-$C_6$ alkyl, $C_3$-$C_6$ cycloalkyl, or optionally substituted phenyl (wherein the substituent(s) is/are selected from halogens, $C_1$-$C_6$ alkyl, cyano and $C_1$-$C_3$ perfluoroalkyl);
$R_2$ can be optionally substituted phenyl (wherein the substituent(s) is/are selected from cyano, acetyl and optionally substituted amino;
$R_3$ can be optionally substituted $C_1$-$C_6$ alkyl or $C_3$-$C_6$ cycloalkyl (wherein the substituent(s) is/are selected from halogens, hydroxyl, $C_1$-$C_3$ alkoxy, and protected hydroxyl); $R_3$ can also be —$NR_6R_7$ wherein $R_6$ and $R_7$ are optionally substituted $C_1$-$C_6$ alkyl (wherein the optional substituent(s) is/are selected from halogens, hydroxyl, $C_1$-$C_3$ alkoxy, and protected hydroxyl).
As used herein the term "alkyl", unless otherwise defined, refers to straight or branched chain hydrocarbon of from 1 to 10 carbon atom(s). Examples of alkyl include, but are not limited to, methyl, ethyl, n-propyl, isopropyl, butyl, octyl, and the like.

Alkyl may optionally be substituted with halogen, hydroxy, protected hydroxyl, $C_1$-$C_3$ alkoxy, optionally substituted amino and $C_1$-$C_6$ alkoxycarbonyl.

As used herein the term "optionally substituted amino", unless otherwise defined, refers to $NR_{14}R_{15}$ wherein $R_{14}$ and $R_{15}$ are independently selected from hydrogen, alkyl, aryl, aralkyl, $C_3$-$C_7$ cycloalkyl, $SO_2R_{16}$, $COR_{16}$, $CONHR_{16}$ and $CSNHR_{16}$ (wherein $R_{16}$ is $C_1$-$C_6$ alkyl, aryl or aralkyl).

As used herein the term "protected hydroxyl" refers to a hydroxy moiety protected by a group $R_{17}$ wherein $R_{17}$ is selected from alkyl, cycloalkyl, aralkyl, aryl, —$(CH_2)_nOR_{18}$ (wherein $R_{18}$ is selected from alkyl, cycloalkyl, aralkyl, aryl and n represents an integer from 1 to 6), $COR_{19}$, $CSR_{19}$, $CONHR_{19}$ and $CSNHR_{19}$ (wherein $R_{19}$ is selected from alkyl, aryl, aralkyl and heterocyclyl). Examples of protected hydroxyl include, but are not limited to, —$OCH_3$, —$OC_2H_5$, —O-n-propyl, —O-i-propyl, —O-cyclopropyl, —O—$CH_2OCH_3$, —O-cyclopentyl, —O-cyclohexyl, —O-benzyl, —O-chlorobenzyl, —O-methoxybenzyl, —O-phenyl, —O-chlorophenyl, —O—$COCH_3$, —O—$COC_2H_5$, —O—CObenzyl, —O—COphenyl, —O—COpyridinyl, —O—CONHphenyl, —O—CONHpyridinyl, —O—CONH-octyl, —O—CSNHphenyl, and the like.

As used herein the term "aralkyl" refers to $(CH_2)_n$aryl wherein n is an integer from 1 to 6.

As used herein the term "aryl", unless otherwise defined, refers to an aromatic radical having 6 to 14 carbon atoms. Examples of aryl include, but are not limited to, phenyl, napthyl, anthryl and biphenyl, and the like.

As used herein the term "heterocyclyl" refers to non-aromatic, aromatic or aromatic fused with non-aromatic ring system having one or more heteroatom (s) in either the aromatic or the non-aromatic part wherein the said hetero atom (s) is/are selected from the group comprising of nitrogen, sulphur and oxygen and the ring system includes mono, bi or tricyclic. Examples of heterocycles include, but not limited to, benzoxazinyl, benzthiazinyl, benzimidazolyl, benzofuranyl, carbazolyl, Indolyl, indolinyl, oxazolyl, phenoxazinyl, pyridyl and phenothiazinyl, and the like.

The said aryl or heterocyclyl may optionally be substituted with one or more substituent(s) independently selected from halogen, hydroxy, nitro, cyano, alkyl, aryl, alkoxy, thioalkyl, cycloalkoxy, optionally substituted amino.

In accordance with yet another aspect, there are provided processes for the preparation of the compounds described herein.

In accordance with another aspect, there is provided a method for treating a mammal suffering from cholesterol related disease, diabetes and related disease, cerebrovascular disease or cardiovascular disease, comprising administering to a mammal a therapeutically effective amount of compounds disclosed herein.

The compounds of the present invention can be used for treating arteriosclerosis, atherosclerosis, hypercholesterolemia, hyperlipidemia, hyperlipoproteinemia, hypertriglyceridemia, hypertension, stroke, ischemia, endothelium dysfunction, peripheral vascular disease, peripheral arterial disease, coronary heart disease, myocardial infarction, cerebral infarction, myocardial microvascular disease, dementia, Alzheimer's disease, osteoporosis and/or osteopenia, angina or resterosis.

DETAILED DESCRIPTION OF THE INVENTION

The compounds described herein may be prepared by techniques well known in the art and familiar to the average synthetic organic chemist. In addition, the compounds of the present invention may be prepared by the following reaction sequences as depicted in Schemes I, Ia, Ib, II, IIa, III, IIIa, and IV. Further compounds which can be useful for treatment of these diseases, and methods for making such compounds, are disclosed in copending U.S. patent application Ser. No. 10/448,770 filed 30 May, 2003, entitled "Substituted Pyrrole Derivatives," and PCT Application No. PCT/IB2004/01754 filed May 28, 2004 entitled "Substituted Pyrrole Derivatives," which applications are incorporated herein in their entirety.

Scheme I

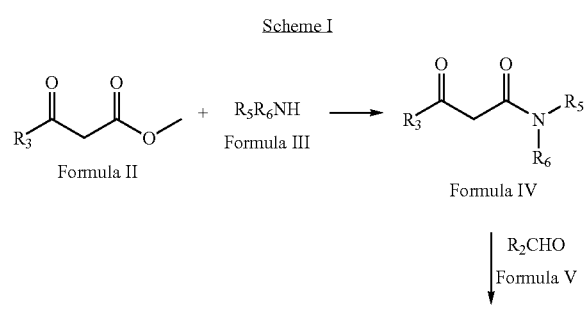

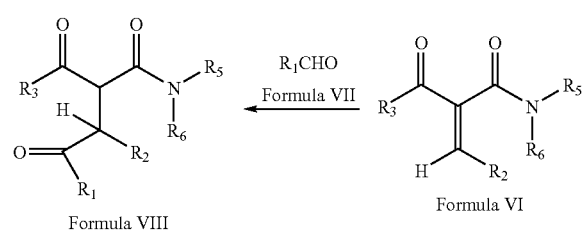

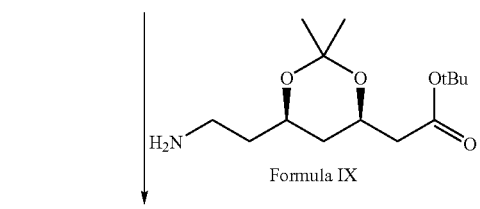

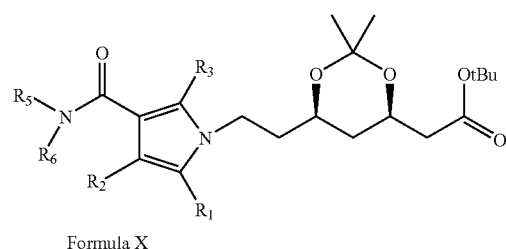

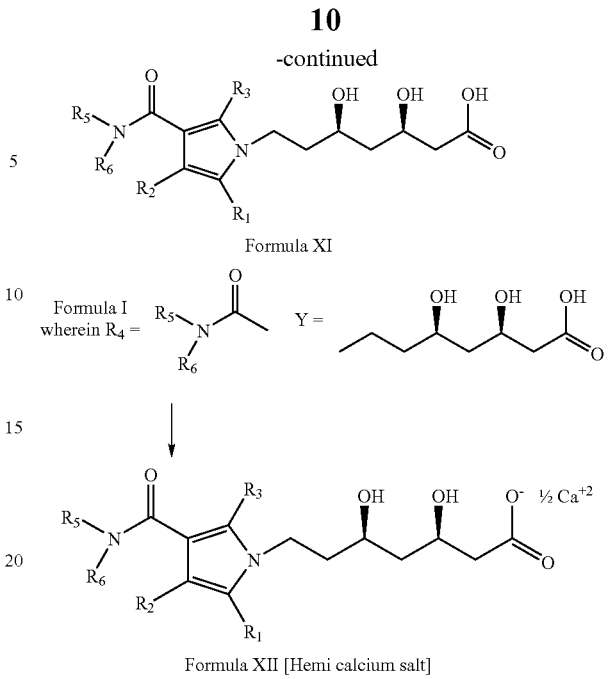

Scheme I

The compound of Formula XII can be prepared according to Scheme I. Accordingly, a compound of Formula II is reacted with a compound of Formula III, wherein $R_3$, $R_5$ and $R_6$ are as defined earlier, to give a compound of Formula IV which on reaction with a compound of Formula V (wherein $R_2$ is as defined earlier) gives a compound of Formula VI, which on treatment with a compound of Formula VII (wherein $R_1$ is as defined earlier) yields a compound of Formula VIII, which on further reaction with a compound of Formula IX gives a compound of Formula X, which on hydrolysis gives a compound of Formula XI, which can then be further converted to hemicalcium salt.

The reaction of a compound of Formula II with a compound of Formula III to give a compound of Formula IV can be carried out in a nonpolar solvent, such as xylene or toluene. The reaction of a compound of Formula II with a compound of Formula III can be carried out in the presence of an organic base, such as triethylamine, pyridine or 1,2-ethylenediamine. The reaction of a compound of Formula IV with an aldehyde of Formula V to give a compound of Formula VI can be carried out in a nonpolar solvent such as hexane, heptane, dichloromethane or toluene or mixture(s) thereof. The reaction of a compound of Formula IV with an aldehyde of Formula V can be carried out in the presence of an organic base such as piperidine, pyridine or β-alanine and an organic acid such as glacial acetic acid or benzoic acid. The reaction of a compound of Formula VI with an aldehyde of Formula VII to give a compound of Formula VIII can be carried out in the presence of a suitable catalyst, such as sodium cyanide, 3-ethyl-5-(2-hydroxyethyl)-4-methyl thiazolium bromide or 3-benzyl-5-(2-hydroxyethyl)-4-methyl thiazolium chloride, in a solvent free condition or in an alcoholic solvent, such as methanol, ethanol, propanol or isopropanol. The reaction of a compound of Formula VI with an aldehyde of Formula VII can be carried out in the presence of an organic base, such as triethylamine or pyridine.

The reaction of a compound of Formula VIII with a compound of Formula IX to give a compound of Formula X can be carried out in a nonpolar solvent, such as xylene, toluene hexane, heptane, tetrahydrofuran, or a mixture thereof in a suitable ratio. The reaction of a compound of Formula VIII with a compound of Formula IX can be carried out in the presence of an organic acid, such as pivalic acid or p-toluene sulfonic acid.

The conversion of a compound of Formula X to a compound of Formula XI can be carried out in a two-step manner, involving an initial acid-catalysed cleavage of ketal, followed by base-catalysed hydrolysis of the tert-butyl ester. The acid can be a mineral acid, such as hydrochloric acid. The cleavage of ketal can be carried out by any other cleavage method known in the prior art. The base can be an organic base, such as lithium hydroxide, sodium hydroxide or potassium hydroxide.

The compound of Formula XI can be converted into its corresponding hemi calcium salt by following procedures well-known to a person ordinary skilled in the art. The hemi calcium salts of compound of Formula XI can also be prepared from the corresponding lactones form of Formula XI by following procedures well-known in the art.

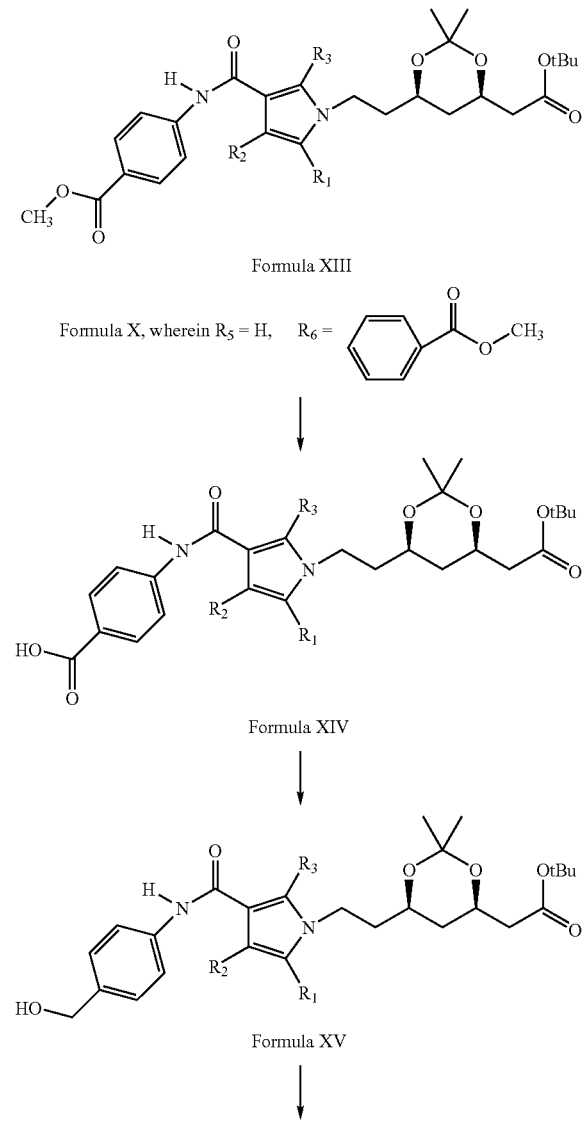

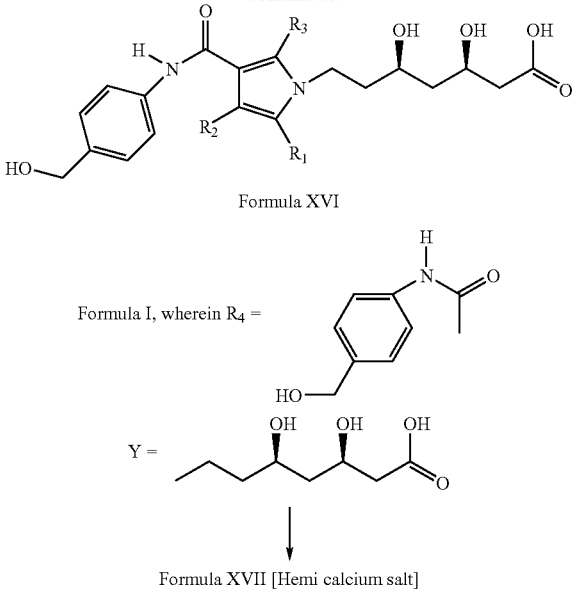

Scheme Ia

The compound of Formula XVII can be prepared according to Scheme Ia. Accordingly, a compound of Formula XIII (that is, Formula X wherein $R_5$=H and

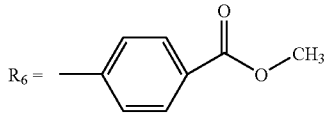

prepared according to Scheme I) is hydrolyzed to give a compound of Formula XIV which, on reduction, gives a compound of Formula XV, which on hydrolysis gives a compound of Formula XVI, which can then be further converted to hemi calcium salt.

The hydrolysis of a compound of Formula XIII to give a compound of Formula XIV can be carried out in a polar solvent, such as tetrahydrofuran, dioxane, methanol, ethanol or mixture(s) thereof. The hydrolysis of a compound of Formula XIII can be carried out in the presence of an inorganic base such as lithium hydroxide, sodium hydroxide or potassium hydroxide.

The reduction of a compound of Formula XIV to give a compound of Formula XV can be carried out in the presence of iodine and a reducing agent, such as sodium borohydride or borane dimethylsulphide in an organic solvent, such as tetrahydrofuran, dioxane or diethylether.

The conversion of a compound of Formula XV to a compound of Formula XVI is carried out in a two-step manner, involving an initial acid-catalyzed cleavage of ketal, followed by base-catalyzed hydrolysis of the tert-butyl ester. The acid can be a mineral acid, such as hydrochloric acid. The cleavage of ketal can be carried out by any other cleavage method known in the prior art. The base can be an inorganic base, such as lithium hydroxide, sodium hydroxide or potassium hydroxide.

The compound of Formula XVI can be converted into its corresponding hemi calcium salt by following procedures well-known to a person ordinary skilled in the art. The hemi calcium salts of compound of Formula XVI can also be prepared from the corresponding lactone form of Formula XVI by following procedures well-known in the art.

Scheme Ib
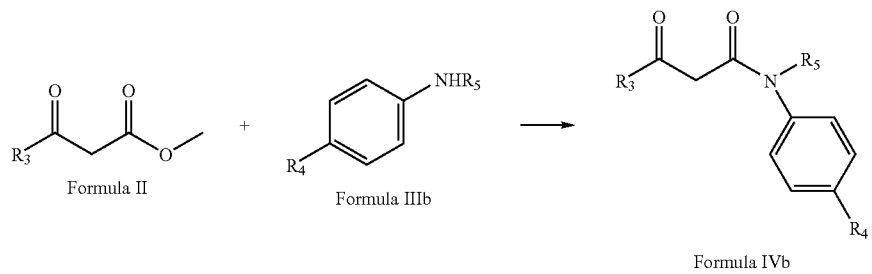
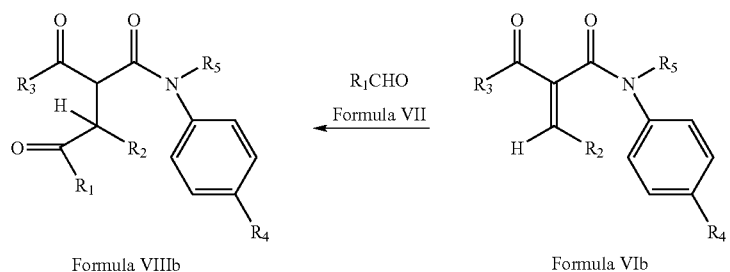
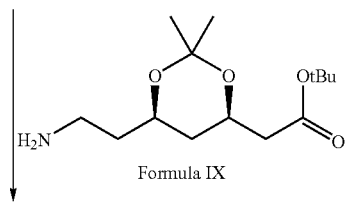
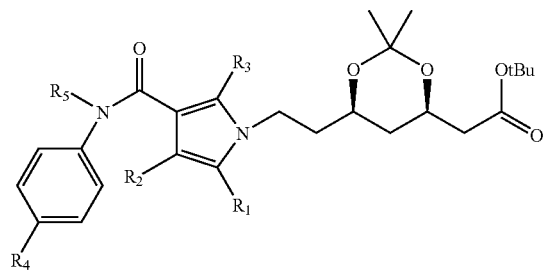

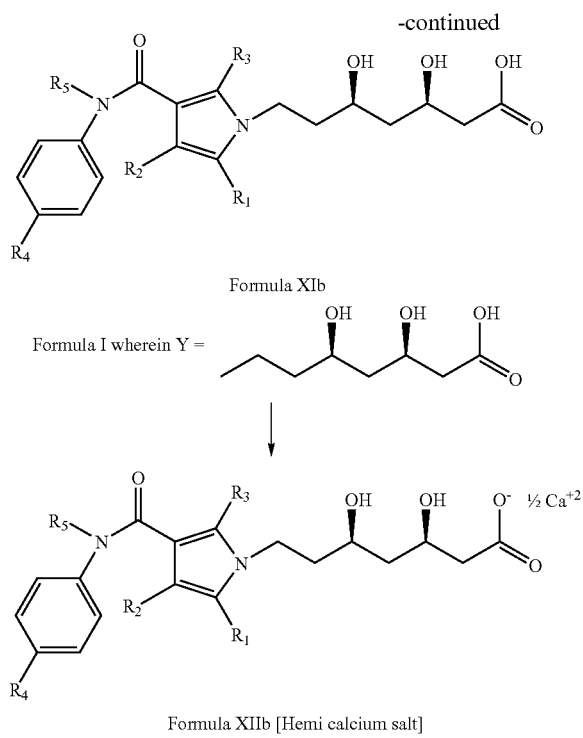

Formula XIIb [Hemi calcium salt]

Scheme Ib

The compound of Formula XIIb can be prepared according to Scheme Ib. Accordingly, a compound of Formula II is reacted with a compound of Formula IIIb, wherein $R_3$, $R_4$ and $R_5$ are as defined earlier, to give a compound of Formula IVb which on reaction with a compound of Formula V (wherein $R_2$ is as defined earlier) gives a compound of Formula VIb, which on treatment with a compound of Formula VII (wherein $R_1$ is as defined earlier) yields a compound of Formula VIIIb, which on further reaction with a compound of Formula IX gives a compound of Formula Xb, which on hydrolysis gives a compound of Formula XIb, which can then be further converted to hemicalcium salt.

The reaction of a compound of Formula II with a compound of Formula IIIb to give a compound of Formula IVb can be carried out in an aromatic solvent, such as xylene or toluene. The reaction of a compound of Formula II with a compound of Formula IIIb can be carried out in the presence of an organic base, such as triethylamine, pyridine or 1,2-ethylenediamine.

The reaction of a compound of Formula IVb with an aldehyde of Formula V to give a compound of Formula VIb can be carried out in a hydrocarbon solvent, such as hexane, heptane, or halogenated solvent, such as dichloromethane, or aromatic solvent, such as toluene, or mixture thereof. The reaction of a compound of Formula IVb with an aldehyde of Formula V can be carried out in the presence of an organic base such as piperidine, pyridine or β-alanine and an organic acid such as glacial acetic acid or benzoic acid.

The reaction of a compound of Formula VIb with an aldehyde of Formula VII to give a compound of Formula VIIIb can be carried out in the presence of a suitable catalyst, such as sodium cyanide, 3-ethyl-5-(2-hydroxyethyl)-4-methyl thiazolium bromide or 3-benzyl-5-(2-hydroxyethyl)-4-methyl thiazolium chloride, in a solvent free condition or in an alcoholic solvent, such as methanol, ethanol, propanol or isopropanol or ethers, such as dioxan or tetrahydrofuran. The reaction of a compound of Formula VIb with an aldehyde of Formula VII can be carried out in the presence of an organic base, such as triethylamine or pyridine.

The reaction of a compound of Formula VIIIb with a compound of Formula IX to give a compound of Formula Xb can be carried out in a solvent, such as xylene, toluene, hexane, heptane, tetrahydrofuran, or a mixture thereof in a suitable ratio. The reaction of a compound of Formula VIIIb with a compound of Formula IX can be carried out in the presence of an organic acid, such as pivalic acid or p-toluene sulfonic acid.

The conversion of a compound of Formula Xb to a compound of Formula XIb can be carried out in a two-step manner, involving an initial acid-catalysed cleavage of ketal, followed by base-catalysed hydrolysis of the tert-butyl ester. The acid can be a mineral acid, such as hydrochloric acid. The cleavage of ketal can be carried out by any other cleavage method known in the prior art. The base can be an inorganic base, such as lithium hydroxide, sodium hydroxide or potassium hydroxide.

The compound of Formula XIb can be converted into its corresponding hemi calcium salt by following procedures well-known to a person ordinary skilled in the art. The hemi calcium salts of compound of Formula XIb can also be prepared from the corresponding lactones form of Formula XIb by following procedures well-known in the art.

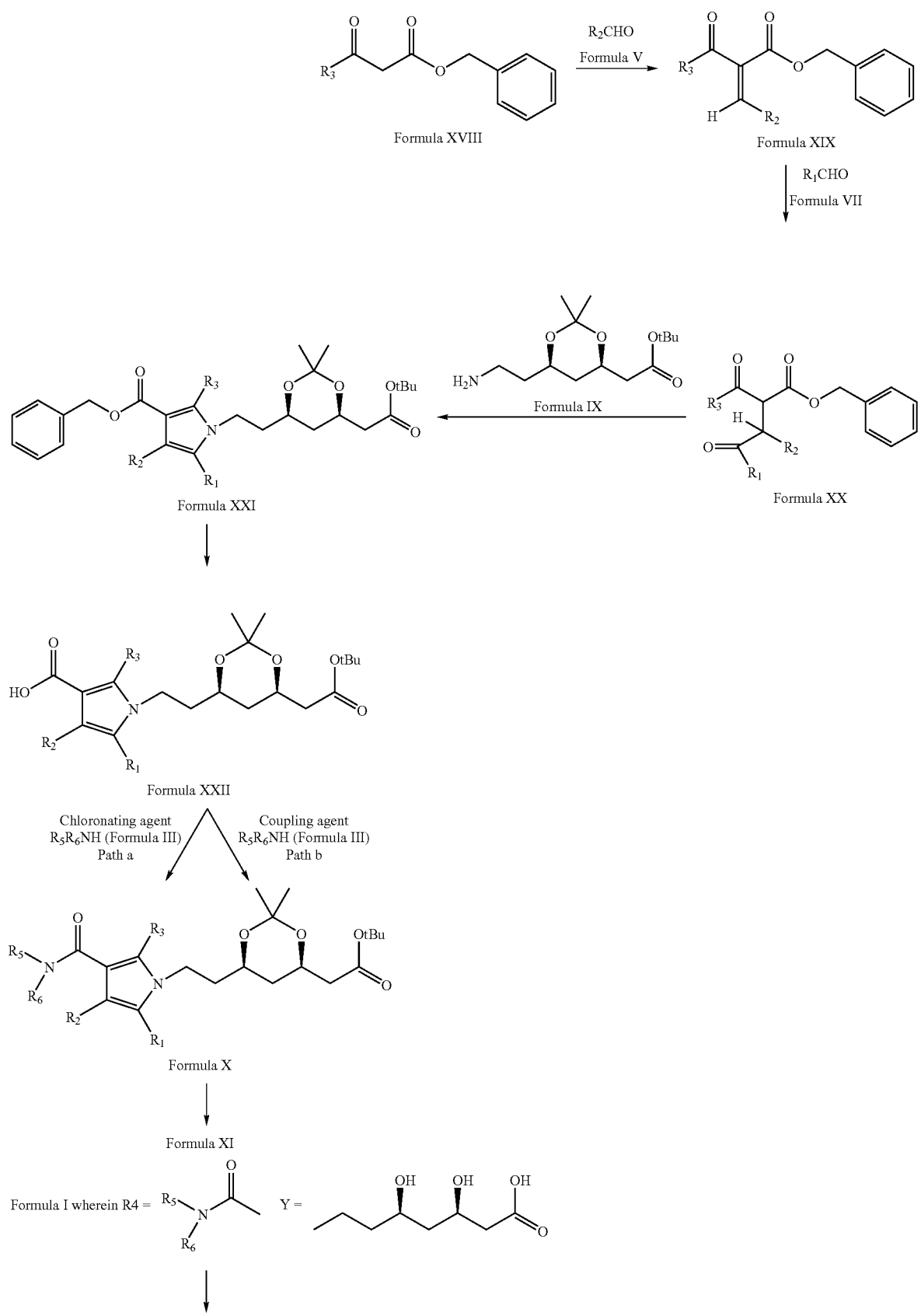

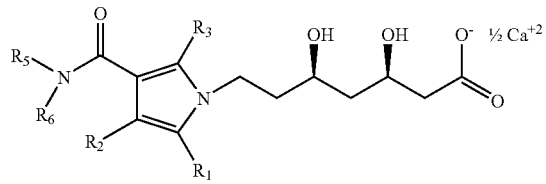

Formula XII [Hemi calcium salt]

Scheme II

The compound of Formula XII can also be prepared according to Scheme II. Accordingly, a compound of Formula XVIII is reacted with a compound of Formula V to give a compound of Formula XIX (wherein $R_2$ and $R_3$ are as defined earlier in Scheme I) which on reaction with a compound of Formula VII (wherein $R_1$ is as defined earlier) gives a compound of Formula XX, which on treatment with a compound of Formula IX yields a compound of Formula XXI, which on debenzylation gives a compound of Formula XXII, which on (a) conversion to corresponding acid chloride followed by reaction with an amine of Formula III (Path a) or (b) reaction with an amine of Formula III in the presence of a coupling agent (Path b), gives a compound of Formula X, which on hydrolysis gives a compound of Formula XI, which can be further converted to hemicalcium salt of Formula XI by following the procedure well known in the art.

The reaction of a compound of Formula XVIII with an aldehyde of Formula V to give a compound of Formula XIX can be carried out in a nonpolar solvent, such as xylene, toluene, heptane, hexane or dichloromethane or mixture thereof. The reaction of a compound of Formula XVIII with a compound of Formula V can be carried out in the presence of an organic base, such as triethylamine, pyridine, piperidine or β-alanine and an organic acid such as glacial acetic acid or benzoic acid.

The reaction of a compound of Formula XIX with an aldehyde of Formula VII to give a compound of Formula XX can be carried out in a polar solvent, such as an alcoholic solvent, for example, methanol, ethanol, propanol or isopropanol. The reaction of a compound of Formula XIX with an aldehyde of Formula VII can be carried out in the presence of an organic base, such as triethylamine or pyridine. The reaction of a compound of Formula XIX with an aldehyde of Formula VII to give a compound of Formula XX can be carried out in the presence of a catalyst, such as sodium cyanide, 3-ethyl-5-(2-hydroxyethyl)-4-methyl thiazolium bromide or 3-benzyl-5-(2-hydroxyethyl)-4-methyl thiazolium chloride.

The reaction of a compound of Formula XX with an amine of Formula IX to give a compound of Formula XXI can be carried out in the presence of an acid, such as pivalic acid and p-toluene sulfonic acid in a nonpolar solvent such as hexane, heptane, toluene or tetrahydrofuran.

The debenzylation of a compound of Formula XXI to give a compound of Formula XXII can be carried out in the presence of a catalyst, such as palladium on carbon and hydrogen, in a polar solvent, such as methanol, ethanol, propanol or dioxane.

The conversion of compound of Formula XXII to its corresponding acid chloride (Path a) can be carried out with any suitable chlorinating agent, such as oxalyl chloride, in a nonpolar solvent, such as benzene, dichloromethane, tetrahydrofuran, toluene or xylene, followed by reaction with an amine of Formula III to give a compound of Formula X, in a non-polar solvent, such as benzene, and in the presence of an organic base, such as triethylamine or pyridine.

Reaction of compound of Formula XXII with an amine of Formula III to give a compound of Formula X can be carried out in the presence of a coupling agent (Path b), such as O-benzotriazol-1-yl-N,N,N',N'-tetramethyl uronium hexafluorophosphate (HBTU), bis(2-oxo-3-oxazolidinyl) phosphine (BOP), 1,3-dicyclohexylcarbodiimide (DCC), 2-(1H-benzotriazole-1-yl)-1,1,3,3-tetramethyluronium tetrafluoroborate (TBTU), benzotriazole-1-yl-oxy-tris-pyrrolidino-phosphonium hexafluorophosphate (PyBOP) or carbonyldiimidazole (CDI) in a polar solvent, such as dimethylformamide, and an organic base, such as diisopropylethyl amine.

The conversion of a compound of Formula X to a compound of Formula XI can be carried out in a two-step manner, involving an initial acid-catalysed cleavage of ketal, followed by base-catalysed hydrolysis of the tert-butyl ester. The acid can be a mineral acid, such as hydrochloric acid. The cleavage of ketal can be carried out by any other cleavage method known in the prior art. The base can be an inorganic base, for example, lithium hydroxide, sodium hydroxide or potassium hydroxide.

The compound of Formula XI can be converted into its corresponding hemi calcium salt by following procedures well-known to a person ordinary skilled in the art. The hemi calcium salts of compound of Formula XI can also be prepared from the corresponding lactone form of Formula XI by following procedures well-known in the art.

Scheme IIa

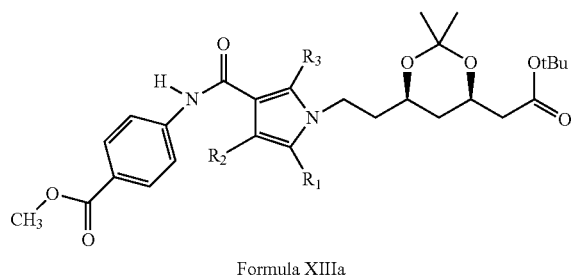

Formula XIIIa

Formula X, wherein $R_5$ = H,

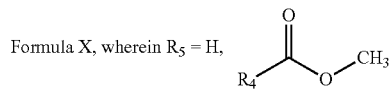

-continued

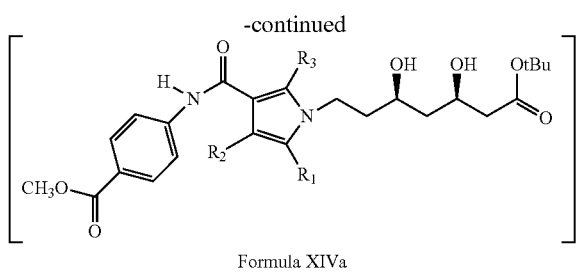

Formula XIVa

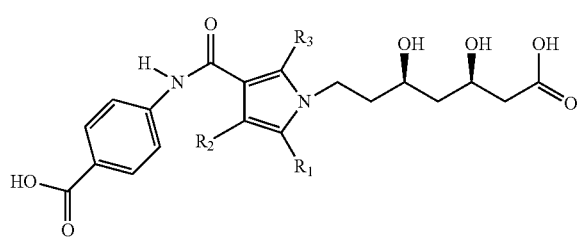

Formula XVa
Formula I, wherein R$_4$ = —COOH, R$_5$ = H,

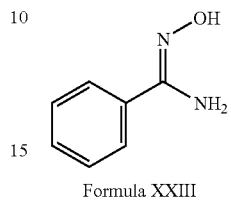

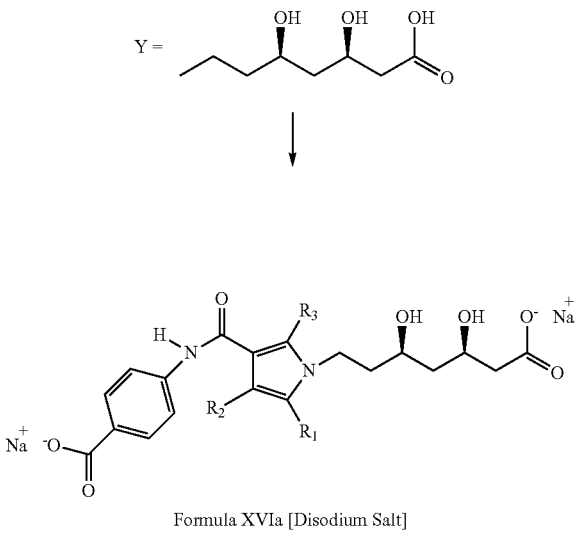

Formula XVIa [Disodium Salt]

Scheme IIa

The compound of Formula XVIa can be prepared according to Scheme IIa. Accordingly, a compound of Formula XIIIa (that is, Formula Xa wherein R$_5$=H and R$_4$=—COOCH$_3$, prepared according to Scheme I) is hydrolyzed to give a compound of Formula XIVa, which on further hydrolysis gives a compound of Formula XVa, which can then be converted to disodium salt.

The conversion of compounds of Formula XIIIa to compounds of Formula XVa can be carried out in a two-step manner, involving an initial acid-catalyzed cleavage of ketal, followed by base-catalyzed hydrolysis of the methyl and tert-butyl ester. The acid can be a mineral acid, such as hydrochloric acid. The cleavage of ketal can be carried out by any other cleavage method known in the prior art. The base can be an inorganic base, such as lithium hydroxide, sodium hydroxide or potassium hydroxide.

The compound of Formula XVa can be converted into its corresponding disodium salt by following procedures well-known to a person ordinary skilled in the art.

Scheme III

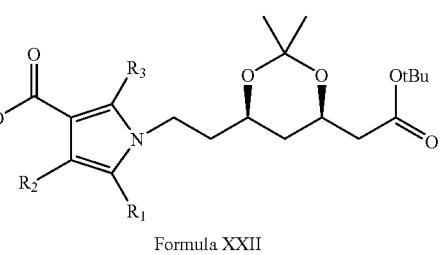

Formula XXIII

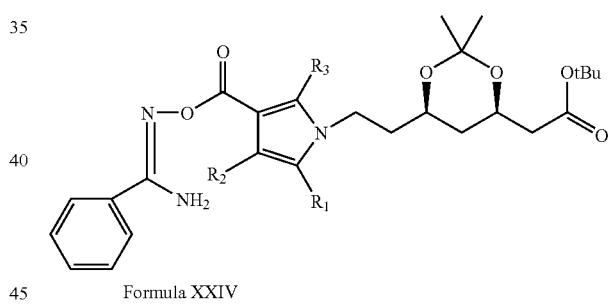

Formula XXII

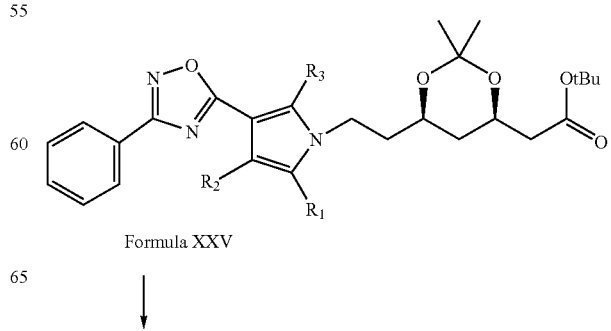

Formula XXIV

Formula XXV

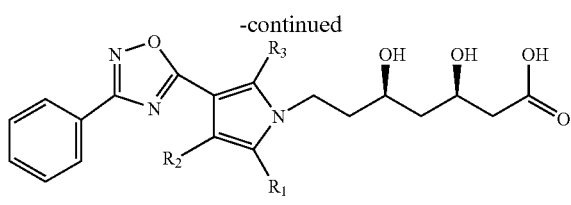

Formula XXVI

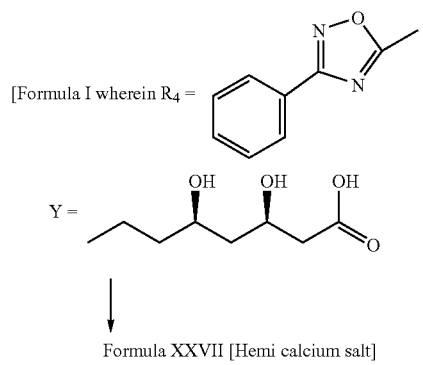

Formula XXVII [Hemi calcium salt]

Scheme III

The compound of Formula XXVII can be prepared according to Scheme III. Amidoxime (prepared as per procedure described in *J. Med. Chem.*, 45:944 (2002) and *J. Med. Chem.*, 29:2174 (1986)) of Formula XXIII on coupling with a compound of Formula XXII (prepared following the steps of Scheme II) gives a compound of Formula XXIV, which on cyclisation in diglyme gives a compound of Formula XXV, which on hydrolysis gives a compound of Formula XXVI, which can be further converted to its hemi calcium salt.

The coupling of compound of Formula XXIII with a compound of Formula XXII can be carried out in the presence of N,N'-carbonyldiimidazole in an organic solvent, such as tetrahydrofuran, dioxane or ether.

The cyclisation of compound of Formula XXIV can be carried out in diglyme to give a compound of Formula XXV.

The conversion of a compound of Formula XXV to a compound of Formula XXVI can be carried out in a two-step manner, involving an initial acid-catalyzed cleavage of ketal, followed by base-catalyzed hydrolysis of the tert-butyl ester. The acid can be a mineral acid, such as hydrochloric acid. The cleavage of ketal can be carried out by any other cleavage method known in the prior art. The base can be an inorganic base, for example, lithium hydroxide, sodium hydroxide or potassium hydroxide.

The compound of Formula XXVI can be converted into its corresponding hemi calcium salt by following procedures well-known to a person ordinary skilled in the art. The hemi calcium salts of compound of Formula XXVI can also be prepared from the corresponding lactone form of Formula XXVI by following procedures well-known in the art.

Scheme IIIa

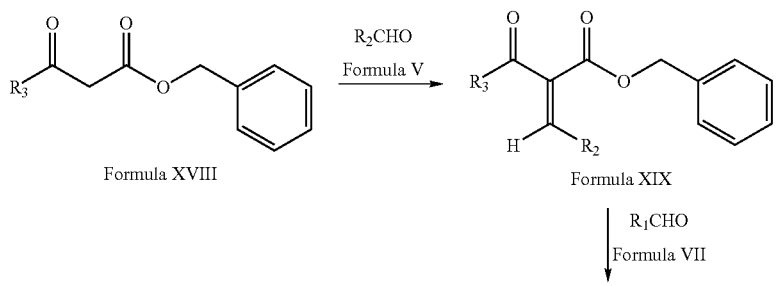

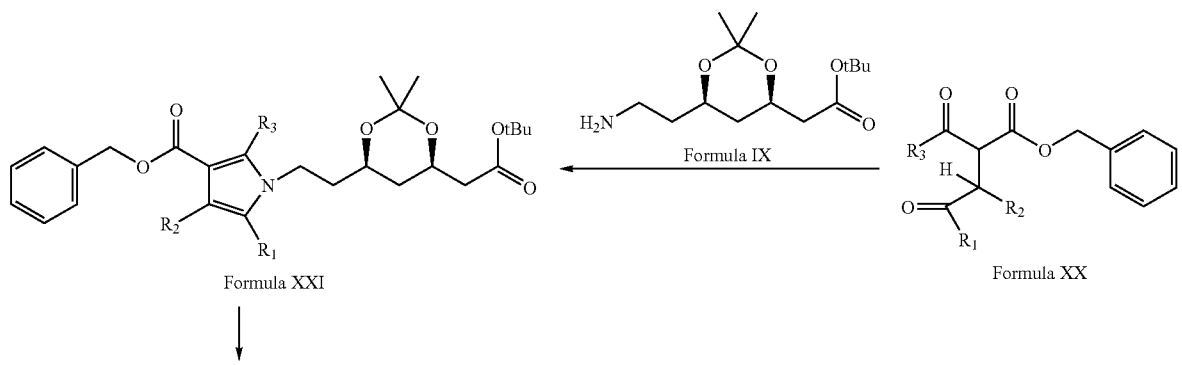

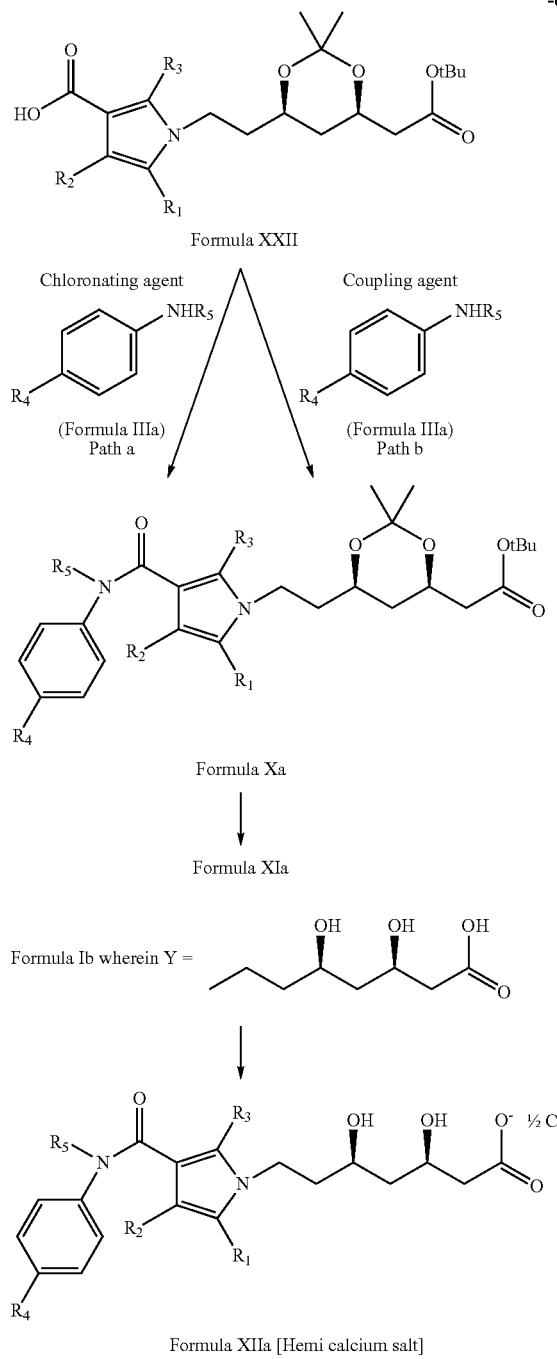

Scheme IIIa

The compound of Formula XIIa can also be prepared according to Scheme IIIa. Accordingly, a compound of Formula XVIII is reacted with a compound of Formula V to give a compound of Formula XIX (wherein $R_2$ and $R_3$ are as defined earlier) which on reaction with a compound of Formula VII (wherein $R_1$ is as defined earlier) gives a compound of Formula XX, which on treatment with a compound of Formula IX yields a compound of Formula XXI, which on debenzylation gives a compound of Formula XXII, which on (a) conversion to corresponding acid chloride followed by reaction with an amine of Formula IIIa (Path a) or (b) reaction with an amine of Formula IIIa in the presence of a coupling agent (Path b) gives a compound of Formula Xa, which on hydrolysis gives a compound of Formula XIa, which can be further converted to hemi calcium salt of Formula XIa by following the procedure well known in the art.

The reaction of a compound of Formula XVIII with an aldehyde of Formula V to give a compound of Formula XIX can be carried out in a hydrocarbon solvent, such as hexane or heptane, or halogenated solvent, such as dichloromethane, or aromatic solvent, such as toluene or xylene, or mixture thereof. The reaction of a compound of Formula XVIII with a compound of Formula V can be carried out in the presence of an organic base, such as triethylamine, pyridine, piperidine or β-alanine and an organic acid such as glacial acetic acid or benzoic acid.

The reaction of a compound of Formula XIX with an aldehyde of Formula VII to give a compound of Formula XX can be carried out in a polar solvent, such as an alcoholic solvent, for example, methanol, ethanol, propanol or isopropanol. The reaction of a compound of Formula XIX with an aldehyde of Formula VII can be carried out in the presence of an organic base, such as triethylamine or pyridine. The reaction of a compound of Formula XIX with an aldehyde of Formula VII to give a compound of Formula XX can be carried out in the presence of a catalyst, such as sodium cyanide, 3-ethyl-5-(2-hydroxyethyl)-4-methyl thiazolium bromide or 3-benzyl-5-(2-hydroxyethyl)-4-methyl thiazolium chloride.

The reaction of a compound of Formula XX with an amine of Formula IX to give a compound of Formula XXI can be carried out in the presence of an acid, such as pivalic acid and p-toluene sulfonic acid in a hydrocarbon solvent, such as hexane or heptane, or aromatic solvent, such as toluene, or ether, such as tetrahydrofuran or mixture thereof.

The debenzylation of a compound of Formula XXI to give a compound of Formula XXII can be carried out in the presence of a catalyst, such as palladium on carbon and hydrogen, in a polar solvent, such as alcoholic solvent, for example, methanol, ethanol or propanol, or ether solvent, for example, dioxane.

The conversion of compound of Formula XXII to its corresponding acid chloride (Path a) can be carried out with any suitable chlorinating agent, such as oxalyl chloride or thionyl chloride, in an aromatic solvent, such as benzene, toluene or xylene, or halogenated solvent, such as dichloromethane, or ether, such as tetrahydrofuran, followed by reaction with an amine of Formula IIIa to give a compound of Formula Xa, in an aromatic solvent, such as benzene, and in the presence of an organic base, such as triethylamine or pyridine.

Reaction of compound of Formula XXII with an amine of Formula IIIa to give a compound of Formula Xa (path b) can be carried out in the presence of a coupling agent, such as O-benzotriazol-1-yl-N,N,N',N'-tetramethyl uronium hexafluorophosphate (HBTU), bis(2-oxo-3-oxazolidinyl) phosphine (BOP), 1,3-dicyclohexylcarbodiimide (DCC), 2-(1H-benzotriazole-1-yl)-1,1,3,3-tetramethyluronium tetrafluoroborate (TBTU), benzotriazole-1-yl-oxy-tris-pyrrolidino-phosphonium hexafluorophosphate (PyBOP) or carbonyldiimidazole (CDI) in a polar solvent, such as dimethylformamide, and an organic base, such as diisopropylethylamine.

The conversion of a compound of Formula Xa to a compound of Formula XIa can be carried out in a two-step manner, involving an initial acid-catalysed cleavage of ketal, followed by base-catalysed hydrolysis of the tert-butyl ester. The acid can be a mineral acid, such as hydrochloric acid. The cleavage of ketal can be carried out by any other cleavage method known in the prior art. The base can be an inorganic base, for example, lithium hydroxide, sodium hydroxide or potassium hydroxide.

The compound of Formula XIa can be converted into its corresponding hemi calcium salt by following procedures well-known to a person ordinary skilled in the art.

The hemi calcium salts of compound of Formula XIa can also be prepared from the corresponding lactones form of Formula XIa by following procedures well-known in the art.

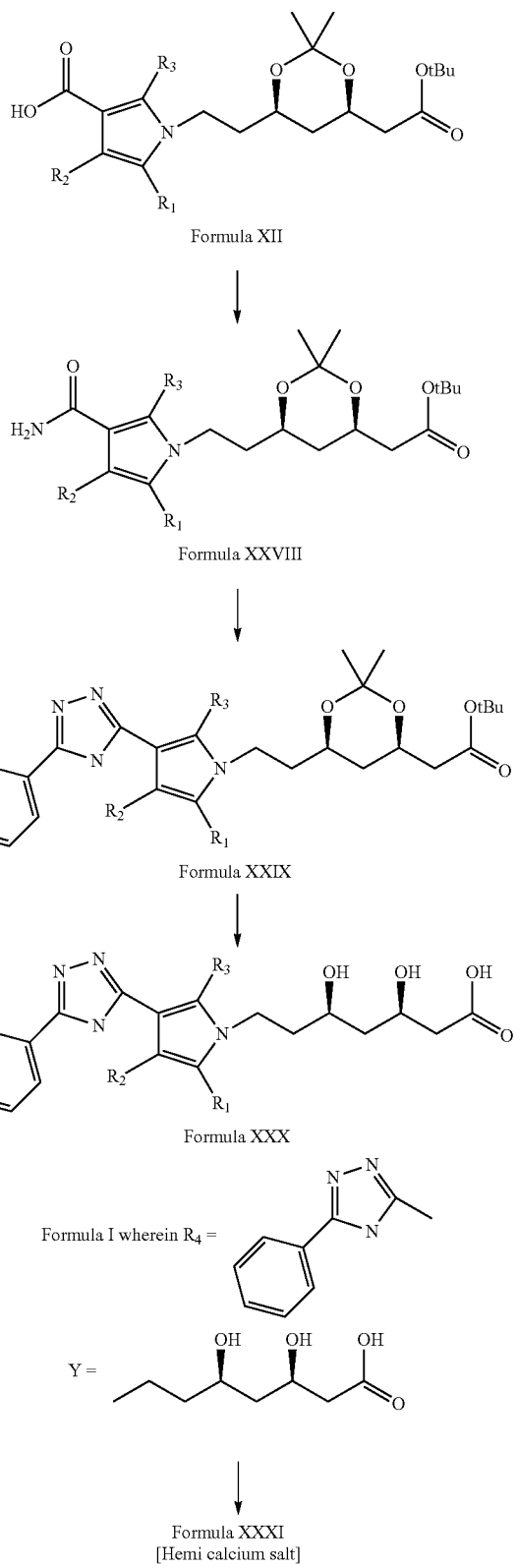

Scheme IV

The compound of Formula XXXI can be prepared according to Scheme IV. Accordingly, treating acid chloride of compound of Formula XXII with ammonia affords a compound of Formula XXVIII, which on condensation with N,N-diethylbenzamide dimethylketal followed by treatment with hydrazine hydrate gives a compound of Formula XXIX, which on hydrolysis gives a compound of Formula XXX, which can be further converted to its hemi calcium salt.

The reaction of compound of Formula XXII to give compound of Formula XXVIII can be carried out in presence of a chlorinating agent, such as oxalyl chloride or thionyl chloride followed by reaction with ammonia.

The condensation of a compound of Formula XXVIII with N,N-dimethylbenzamide dimethylacetal followed by treatment with hydrazine hydrate affords compound of Formula XXIX.

The conversion of a compound of Formula XXIX to a compound of Formula XXX can be carried out in a two-step manner, involving an initial acid-catalyzed cleavage of ketal, followed by base-catalyzed hydrolysis of the tert-butyl ester. The acid can be a mineral acid, such as hydrochloric acid. The cleavage of ketal can be carried out by any other cleavage method known in the prior art. The base can be an inorganic base, for example, lithium hydroxide, sodium hydroxide or potassium hydroxide.

The compound of Formula XXX can be converted into its corresponding hemi calcium salt by following procedures well-known to a person ordinary skilled in the art. The calcium salts of compound of Formula XXX can also be prepared from the corresponding lactone form of Formula XXX by following procedures well-known in the art.

In the above schemes, where specific reagents, such as particular bases, reducing agents, solvents, etc., are mentioned, it is to be understood that other bases, reducing agents, solvents, etc., known to those skilled in the art may be used. Similarly, the reaction temperature and duration may be adjusted according to the desired needs.

An illustrative list of particular compounds disclosed herein is given below (also shown in Table I):

(3R,5R)-7-[2-(4-fluorophenyl)-5-isopropyl-3-phenyl-4-[(2-acetylphenylamino)carbonyl]-pyrrol-1-yl]-3,5-dihydroxy-heptanoic acid (Compound No. 1)

(3R,5R)-7-[2-(4-fluorophenyl)-5-isopropyl-3-phenyl-4-[(3-acetylphenylamino)carbonyl]-pyrrol-1-yl]-3,5-dihydroxy-heptanoic acid (Compound No. 2)

(3R,5R)-7-[2-(4-fluorophenyl)-5-isopropyl-3-phenyl-4-[(4-acetylphenylamino)carbonyl]-pyrrol-1-yl]-3,5-dihydroxy-heptanoic acid (Compound No. 3)

(3R,5R)-7-[2-(4-fluorophenyl)-5-isopropyl-3-phenyl-4-[(2,4-dimethylphenylamino)carbonyl]-pyrrol-1-yl]-3,5-dihydroxy-heptanoic acid (Compound No. 4)

(3R,5R)-7-[2-(4-fluorophenyl)-5-isopropyl-3-phenyl-4-[(cyclohexylamino)carbonyl)]-pyrrol-1-yl]-3,5-dihydroxy-heptanoic acid (Compound No. 5)

(3R,5R)-7-[2-(4-fluorophenyl)-5-isopropyl-3-phenyl-4-[(4-trifluoromethylbenzylamino)carbonyl)]-pyrrol-1-yl]-3,5-dihydroxy-heptanoic acid (Compound No. 6)

(3R,5R)-7-[2-(4-fluorophenyl)-5-isopropyl-3-phenyl-4-(morpholine-4-carbonyl)-pyrrol-1-yl]-3,5-dihydroxy-heptanoic acid (Compound No. 7)

(3R,5R)-7-[2-(4-fluorophenyl)-5-isopropyl-3-phenyl-4-(piperidine-1-carbonyl)-pyrrol-1-yl]-3,5-dihydroxy-heptanoic acid (Compound No. 8)

(3R,5R)-7-[2-(4-fluorophenyl)-5-isopropyl-3-phenyl-4-[(4-hydroxymethylphenylamino)carbonyl]-pyrrol-1-yl]-3,5-dihydroxy-heptanoic acid (Compound No. 11)

(3R,5R)-7-[2-(4-fluorophenyl)-5-isopropyl-3-phenyl-4-[(4-methanesulfonylaminophenyl amino)carbonyl]-pyrrol-1-yl]-3,5-dihydroxy-heptanoic acid (Compound No. 12)

(3R,5R)-7-[2-(4-fluorophenyl)-5-isopropyl-3-phenyl-4-[(4-acetylaminophenylamino)carbonyl]-pyrrol-1-yl]-3,5-dihydroxy-heptanoic acid (Compound No. 13)

(3R,5R)-7-[2-(4-fluorophenyl)-5-isopropyl-3-(4-cyanophenyl)-4-[(phenylamino)carbonyl)]-pyrrol-1-yl]-3,5-dihydroxy-heptanoic acid (Compound No. 14)

(3R,5R)-7-[2-(4-fluorophenyl)-5-isopropyl-3-phenyl-4-[4-carboxyphenyl)amino)carbonyl]-pyrrol-1-yl]-3,5-dihydroxy-heptanoic acid (Compound No. 1a), (3R,5R)-7-[2-(4-fluorophenyl)-5-isopropyl-3-phenyl-4-[4-acetoxymethylphenyl)amino)carbonyl]-pyrrol-1-yl]-3,5-dihydroxy-heptanoic acid (Compound No. 2a), (3R,5R)-7-[2-(4-fluorophenyl)-5-isopropyl-3-phenyl-4-[4-phenylthiocarbamoyl oxymethylphenyl)amino)carbonyl]-pyrrol-1-yl]-3,5-dihydroxy-heptanoic acid (Compound No. 3a), (3R,5R)-7-[2-(4-fluorophenyl)-5-isopropyl-3-phenyl-4-[4-propionyloxymethyl phenyl)amino)carbonyl]-pyrrol-1-yl]-3,5-dihydroxy-heptanoic acid (Compound No. 4a), (3R,5R)-7-[2-(4-fluorophenyl)-5-isopropyl-3-phenyl-4-[4-octylcarbamoyloxymethyl phenyl)amino)carbonyl]-pyrrol-1-yl]-3,5-dihydroxy-heptanoic acid (Compound No. 5a), (3R,5R)-7-[2-(4-fluorophenyl)-5-isopropyl-3-phenyl-4-[4-phenylacetoxymethyl phenyl)amino)carbonyl]-pyrrol-1-yl]-3,5-dihydroxy-heptanoic acid (Compound No. 6a), (3R,5R)-7-[2-(4-fluorophenyl)-5-isopropyl-3-phenyl-4-[4-phenylcarbamoyl oxymethyl phenyl)amino)carbonyl]-pyrrol-1-yl]-3,5-dihydroxy-heptanoic acid (Compound No. 7a), (3R,5R)-7-[2-(4-fluorophenyl)-5-isopropyl-3-phenyl-4-[4-benzoyloxymethyl phenyl)amino)carbonyl]-pyrrol-1-yl]-3,5-dihydroxy-heptanoic acid (Compound 8a)

(3R,5R)-7-[2-(4-fluorophenyl)-5-isopropyl-3-phenyl-4-[4-isonicotinoyloxymethyl phenyl)amino)carbonyl]-pyrrol-1-yl]-3,5-dihydroxy-heptanoic acid (Compound No. 9a), (3R,5R)-7-[2-(4-fluorophenyl)-5-isopropyl-3-phenyl-4-[4-ylcarbamoyl oxymethyl phenyl)amino)carbonyl]-1-yl]-3,5-dihydroxy-heptanoic acid (Compound No. 10a), (3R,5R)-7-[2-(4-fluorophenyl)-5-isopropyl-3-phenyl-4-[4-phenylcarbamoyl phenyl)amino)carbonyl]-pyrrol-1-yl]-3,5-dihydroxy-heptanoic acid (Compound No. 11a), (3R,5R)-7-[2-(4-fluorophenyl)-5-isopropyl-3-phenyl-4-[4-cyclohexylcarbamoyl-phenyl)amino)carbonyl]-pyrrol-1-yl]-3,5-dihydroxy-heptanoic acid (Compound No. 12a), (3R,5R)-7-[2-(4-fluorophenyl)-5-isopropyl-3-phenyl-4-[4-methylcarbamoyl)-phenyl)amino)carbonyl]-pyrrol-1-yl]-3,5-dihydroxy-heptanoic acid (Compound No. 13a), (3R,5R)-7-[2-(4-fluorophenyl)-5-isopropyl-3-phenyl-4-[4-benzylcarbamoyl)-phenyl)amino)carbonyl]-pyrrol-1-yl]-3,5-dihydroxy-heptanoic acid (Compound No. 14a), (3R,5R)-7-[2-(4-fluorophenyl)-5-isopropyl-3-phenyl-4-[4-(morpholine-4-carbonyl)-phenyl)amino)carbonyl]-pyrrol-1-yl]-3,5-dihydroxy-heptanoic acid (Compound No. 15), (3R,5R)-7-[2-(4-fluorophenyl)-5-isopropyl-3-phenyl-4-[4-(piperidine-1-carbonyl)-phenyl)amino)carbonyl]-pyrrol-1-yl]-3,5-dihydroxy-heptanoic acid (Compound No. 16), (3R,5R)-7-[2-(4-fluorophenyl)-5-isopropyl-3-phenyl-4-[4-benzylamino phenyl)amino)carbonyl]-pyrrol-1-yl]-3,5-dihydroxy-heptanoic acid (Compound No. 17), (3R,5R)-7-[2-(4-fluorophenyl)-5-isopropyl-3-phenyl-4-[4-(1-hydroxyethyl)phenylamino)carbonyl]-pyrrol-1-yl]-3,5-dihydroxy-heptanoic acid (Compound No. 18), (3R,5R)-7-[2-(4-fluorophenyl)-5-isopropyl-3-phenyl-4-[4-(2-hydroxyethyl)phenylamino)carbonyl]-pyrrol-1-yl]-3,5-dihydroxy-heptanoic acid (Compound No. 19), (3R,5R)-7-[2-(4-fluorophenyl)-5-isopropyl-3-phenyl-4-[4-(3-hydroxypropyl phenylamino)carbonyl]-pyrrol-1-yl]-3,5-dihydroxy-heptanoic acid (Compound No. 20), (3R,5R)-7-[2-(4-fluorophenyl)-5-isopropyl-3-phenyl-4-[4-(3-hydroxypropyl phenylamino)carbonyl]-pyrrol-1-yl]-3,5-dihydroxy-heptanoic acid (Compound No. 21), (3R,5R)-7-[2-(4-fluorophenyl)-5-isopropyl-3-phenyl-4-[(4-ethoxymethyl phenylamino)carbonyl]-pyrrol-1-yl]-3,5-dihydroxy-heptanoic acid (Compound No. 22), (3R,5R)-7-[2-(4-fluorophenyl)-5-isopropyl-3-phenyl-4-[(4-isopropoxymethyl phenylamino)carbonyl]-pyrrol-1-yl]-3,5-dihydroxy-heptanoic acid (Compound No. 23), (3R,5R)-7-[2-(4-fluorophenyl)-5-isopropyl-3-phenyl-4-[(4-propoxymethyl phenylamino)carbonyl]-pyrrol-1-yl]-3,5-dihydroxy-heptanoic acid (Compound No. 24), (3R,5R)-7-[2-(4-fluorophenyl)-5-isopropyl-3-phenyl-4-[(4-methoxymethoxymethylphenylamino)carbonyl]-pyrrol-1-yl]-3,5-dihydroxy-heptanoic acid (Compound No. 25), (3R,5R)-7-[2-(4-fluorophenyl)-5-isopropyl-3-phenyl-4-[(4-cyclohexyloxymethyl phenylamino)carbonyl]-pyrrol-1-yl]-3,5-dihydroxy-heptanoic acid (Compound No. 26), (3R,5R)-7-[2-(4-fluorophenyl)-5-isopropyl-3-phenyl-4-[(4-cyclopentyloxymethyl phenylamino)carbonyl]-pyrrol-1-yl]-3,5-dihydroxy-heptanoic acid (Compound No. 27), (3R,5R)-7-[2-(4-fluorophenyl)-5-isopropyl-3-phenyl-4-[(4-benzyloxymethyl phenylamino)carbonyl]-pyrrol-1-yl]-3,5-dihydroxy-heptanoic acid (Compound No. 28)

(3R,5R)-7-[2-(4-fluorophenyl)-5-isopropyl-3-phenyl-4-[(4-chlorobenzyloxymethyl phenylamino)carbonyl]-pyrrol-1-yl]-3,5-dihydroxy-heptanoic acid (Compound No. 29), (3R,5R)-7-[2-(4-fluorophenyl)-5-isopropyl-3-phenyl-4-[(4-methoxybenzyloxymethyl phenylamino)carbonyl]-pyrrol-1-yl]-3,5-dihydroxy-heptanoic acid (Compound No. 30), (3R,5R)-7-[2-(4-fluorophenyl)-5-isopropyl-3-phenyl-4-[(4-phenoxymethylphenylamino)carbonyl]-pyrrol-1-yl]-3,5-dihydroxy-heptanoic acid (Compound No. 31), (3R,5R)-7-[2-(4-fluorophenyl)-5-isopropyl-3-phenyl-4-[(4-chlorophenoxymethyl phenylamino)carbonyl]-pyrrol-1-yl]-3,5-dihydroxy-heptanoic acid (Compound No. 32), (3R,5R)-7-[2-(4-fluorophenyl)-5-isopropyl-3-phenyl-4-[(4-acetylaminophenylamino)carbonyl]-pyrrol-1-yl]-3,5-dihydroxy-heptanoic acid (Compound No. 33), (3R,5R)-7-[2-(4-fluorophenyl)-5-isopropyl-3-phenyl-4-[(4-benzoylamino phenylamino)carbonyl]-pyrrol-1-yl]-3,5-dihydroxy-heptanoic acid (Compound No. 34), (3R,5R)-7-[2-(4-fluorophenyl)-5-isopropyl-3-phenyl-4-[(4-benzenesulfonylamino phenylamino)carbonyl]-pyrrol-1-yl]-3,5-dihydroxy-heptanoic acid (Compound No. 36)

(3R,5R)-7-[2-(4-fluorophenyl)-5-isopropyl-3-Phenyl-4-[4-(3-phenyl-ureido)-phenylamino)carbonyl]-pyrrol-1-yl]-3,5-dihydroxy-heptanoic acid (Compound No. 37), (3R,5R)-7-[2-(4-fluorophenyl)-5-isopropyl-3-phenyl-4-[4-(3-methyl-ureido)-phenylamino)carbonyl]-pyrrol-1-yl]-3,5-dihydroxy-heptanoic acid (Compound No. 38), (3R,5R)-7-[2-(4-fluorophenyl)-5-isopropyl-3-phenyl-4-[4-(3-benzyl-ureido)-phenylamino)carbonyl]-pyrrol-1-yl]-3,5-dihydroxy-heptanoic acid (Compound No. 39), (3R,5R)-7-[2-(4-fluorophenyl)-5-isopropyl-3-phenyl-4-[4-(3-benzyl-thioureido)-phenylamino)carbonyl]-pyrrol-1-yl]-3,5-dihydroxy-heptanoic acid (Compound No. 40), (3R,5R)-7-[2-(4-fluorophenyl)-5-isopropyl-3-phenyl-4-[4-(3-phenyl-thioureido)-phenylamino)carbonyl]-pyrrol-1-yl]-3,5-dihydroxy-heptanoic acid (Compound No. 41), (3R,5R)-7-[2-(4-fluorophenyl)-5-isopropyl-3-phenyl-4-[4-(3-methyl-thioureido)-phenylamino)carbonyl]-pyrrol-1-yl]-3,5-dihydroxy-heptanoic acid (Compound No. 42), and their pharmaceutically acceptable salts, pharmaceutically acceptable solvates, tautomers, racemates, polymorphs, pure enantiomers, diastereoisomers, metabolites, prodrugs or N-oxides.

An illustrative list of compounds, which can be prepared by following Schemes III and IV is given below (also shown in Table I):

(3R,5R)-7-[2-(4-Fluorophenyl)-5-isopropyl-3-phenyl-4-(3-phenyl-[1,2,4]oxadiazol-5-yl)-pyrrol-1-yl]-3,5-dihydroxy-heptanoic acid (Compound No. 9)

(3R,5R)-7-[2-(4-Fluorophenyl0-5-isopropyl-3-phenyl-4-(5-phenyl-2H-[1,2,4]triazol-3-yl)-pyrrol-1-yl]-3,5-dihydroxy-heptanoic acid (Compound No. 10)

In Tables I and Ia, $R_4$ is the indicated structure, unless otherwise noted.

TABLE I

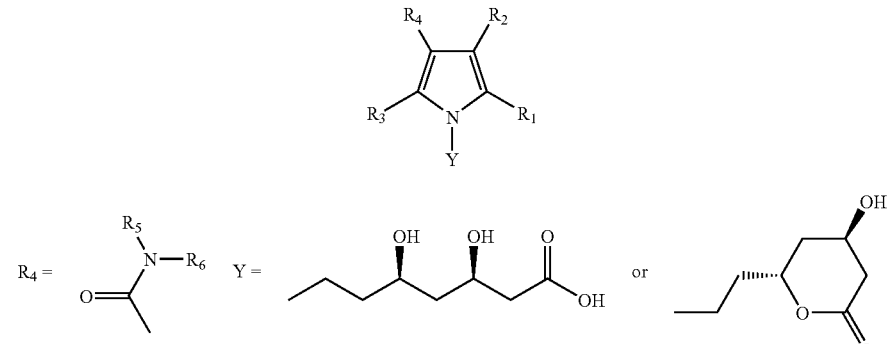

| C. No. | $R_1$ | $R_2$ | $R_3$ | $R_4$ | $R_5$ | $R_6$ |
|---|---|---|---|---|---|---|
| 1 | 4-Fluorophenyl | Phenyl | Isopropyl | — | Hydrogen | 2-Acetylphenyl |
| 2 | 4-Fluorophenyl | Phenyl | Isopropyl | — | Hydrogen | 3-Acetylphenyl |
| 3 | 4-Fluorophenyl | Phenyl | Isopropyl | — | Hydrogen | 4-Acetylphenyl |
| 4 | 4-Fluorophenyl | Phenyl | Isopropyl | — | Hydrogen | 2,4-Dimethylphenyl |
| 5 | 4-Fluorophenyl | Phenyl | Isopropyl | — | Hydrogen | Cyclohexyl |
| 6 | 4-Fluorophenyl | Phenyl | Isopropyl | — | Hydrogen | 4-trifluoromethyl benzyl |
| 7 | 4-Fluorophenyl | Phenyl | Isopropyl | — | | —(CH2)$_2$—O—(CH2)$_2$— |

TABLE I-continued

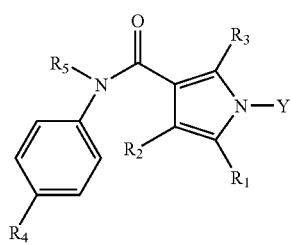

| C. No. | R₁ | R₂ | R₃ | R₄ | R₅ | R₆ |
|---|---|---|---|---|---|---|
| 8 | 4-Fluorophenyl | Phenyl | Isopropyl | — | | —(CH2)₅— |
| 9* | 4-Fluorophenyl | Phenyl | Isopropyl | 1,2,4-Oxadiazinylphenyl | | — |
| 10* | 4-Fluorophenyl | Phenyl | Isopropyl | 1,2,4-Triazolylphenyl | | — |
| 11 | 4-Fluorophenyl | Phenyl | Isopropyl | — | Hydrogen | 4-(Hydroxymethyl)phenyl |
| 12 | 4-Fluorophenyl | Phenyl | Isopropyl | — | Hydrogen | 4-(Methylsulfonamido)-phenyl |
| 13 | 4-Fluorophenyl | Phenyl | Isopropyl | — | Hydrogen | 4-(Acetamido)phenyl |
| 14 | 4-Fluorophenyl | 4-cyanoPhenyl | Isopropyl | — | Hydrogen | Phenyl |

*Hypothetical examples

TABLE Ia

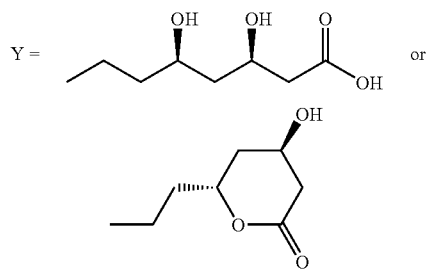

Formula I wherein

R₁ = 4-fluorophenyl, R₂ = phenyl, R₃ = isopropyl, R₅ = hydrogen

| Compound No. | R₄ |
|---|---|
| 1a | COOH |
| 2a | acetoxymethyl |
| 3a | phenylthiocarbamoyloxymethyl |
| 4a | propionyloxymethyl |
| 5a | octylcarbamoyloxymethyl |
| 6a | phenylacetoxymethyl |
| 7a | phenylcarbamoyloxymethyl |
| 8a | benzoyloxymethyl |
| 9a | isonicotinoyloxymethyl |
| 10a | pyridin-4-ylcarbamoyloxymethyl |
| 11a | phenylcarbamoyl |
| 12a | cyclohexylcarbamoyl |

TABLE Ia-continued

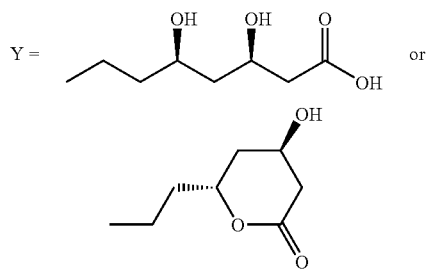

Formula I wherein

R₁ = 4-fluorophenyl, R₂ = phenyl, R₃ = isopropyl, R₅ = hydrogen

| Compound No. | R₄ |
|---|---|
| 13a | methylcarbamoyl |
| 14a | benzylcarbamoyl |
| 15 | morpholine-4-carbonyl |
| 16 | piperidine-1-carbonyl |
| 17 | benzylamino |
| 18 | (1-hydroxyethyl) |
| 19 | (2-hydroxyethyl) |
| 20 | (3-hydroxypropyl) |
| 21 | methoxymethyl |
| 22 | ethoxymethyl |
| 23 | isopropoxymethyl |
| 24 | propoxymethyl |

TABLE Ia-continued

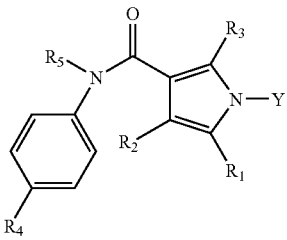

Formula I wherein

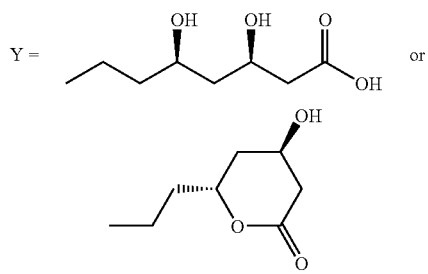

$R_1$ = 4-fluorophenyl, $R_2$ = phenyl, $R_3$ = isopropyl, $R_5$ = hydrogen

| Compound No. | $R_4$ |
|---|---|
| 25 | methoxymethoxymethyl |
| 26 | cyclohexyloxymethyl |
| 27 | cyclopentyloxymethyl |
| 28 | benzyloxymethyl |
| 29 | 4-chlorobenzyloxymethyl |
| 30 | 4-methoxybenzyloxymethyl |
| 31 | phenoxymethyl |
| 32 | 4-chlorophenoxymethyl |
| 33 | acetylamino |
| 34 | Benzoylamino |
| 36 | benzenesulfonylamino |
| 37 | 3-phenyl-ureido |
| 38 | 3-methyl-ureido |
| 39 | 3-benzyl-ureido |
| 40 | 3-benzyl-thioureido |
| 41 | 3-phenyl-thioureido |
| 42 | 3-methyl-thioureido |

The term "pharmaceutically acceptable" means approved by regulatory agency of the federal or a state government or listed in the U.S. Pharmacopeia or other generally recognized pharmacopeia for use in animals, and more particularly in humans.

The term "pharmaceutically acceptable salts" refer to a salt prepared from pharmaceutically acceptable monovalent, divalent or trivalent non-toxic metal or organic base. Examples of such metal salts include, but are not limited to, lithium, sodium, potassium, calcium, magnesium, zinc, aluminum, and the like. Examples of such organic bases include, but are not limited to, amino acid, ammonia, mono-alkyl ammonium, dialkyl ammonium, trialkyl ammonium and N-methyl glucamine and the like. The free acid forms of compounds of the present invention may be prepared from the salt forms, if desired, by contacting the salt with dilute aqueous solution of an acid such as hydrochloric acid. The base addition salts may differ from the free acid forms of the compounds of this invention in such physical characteristics as solubility and melting point.

The term "pharmaceutically acceptable solvates" refers to solvates with water (i-e hydrates) or pharmaceutically acceptable solvents, for example solvates with ethanol and the like. Such solvates are also encompassed within the scope of the disclosure.

Furthermore, some of the crystalline forms for compounds described herein may exist as polymorphs and as such are intended to be included in the scope of the disclosure.

The present invention also includes within its scope prodrugs of these agents. In general, such prodrugs will be functional derivatives of these compounds, which are readily convertible in vivo into the required compound. Conventional procedure for the selection and preparation of suitable prodrug derivatives are described, for example, in "design of prodrugs", ed. H Bundgaard and, Elsevier, 1985.

The present invention also includes metabolites, which become active upon introduction into the biological system.

The compounds of the invention possess two chiral centers, they may, therefore, exist as enantiomers and diastereomers. It is to be understood that all such isomers and racemic mixtures therefore are encompassed within the scope of the present invention. Preferably, this invention contemplates compounds only with 3R and 5R configuration.

The crystalline or amorphous forms of compounds disclosed herein may exist as polymorphs and as such are intended to be included in the present invention.

Pharmaceutical compositions comprising compounds disclosed herein, their pharmaceutically acceptable salt, pharmaceutically acceptable solvates, or polymorphs, and pharmaceutically acceptable carrier or excipient are also disclosed herein.

The compositions provided herein, both those containing one disclosed compound and those containing two or more compounds, may be suitable for oral or parenteral administration. The compositions may be formulated to provide immediate or sustained release of the therapeutic compounds. The compounds described herein can be administered alone but will generally be administered as an admixture with a suitable pharmaceutically acceptable carrier. The term "pharmaceutically acceptable carrier" is intended to include non-toxic, inert solid, semi-solid, liquid filter, diluent, encapsulating materials or formulation auxiliaries of any type.

Solid form preparations for oral administration may include capsules, tablets, pills, powder, granules or suppositories. For solid form preparations, the active compound is mixed with at least one inert, pharmaceutically acceptable excipient or carrier, for example, sodium citrate, dicalcium phosphate and/or a filler, an extender, for example, starch, lactose, sucrose, glucose, mannitol or silicic acid; binders, for example, carboxymethyl cellulose, alginates, gelatins, polyvinylpyrrolidinone, sucrose, or acacia; disintegrating agents, for example, agar-agar, calcium carbonate, potato starch, aliginic acid, certain silicates or sodium carbonate; absorption accelerators, for example, quaternary ammonium compounds; wetting agents, for example, cetyl alcohol, glycerol, or mono stearate adsorbents, for example, Kaolin; lubricants, for example, talc, calcium stearate, magnesium stearate, solid polyethyleneglycol, or sodium lauryl sulphate, and mixtures thereof.

In case of capsules, tablets, and pills, the dosage form may also comprise buffering agents.

The solid preparation of tablets, capsules, pills, or granules can be accomplished with coatings and/or shells, for example, enteric coatings and other coatings well known in the pharmaceutical formulating art.

Liquid form preparations for oral administration can include pharmaceutically acceptable emulsions, solutions, suspensions, syrups and elixirs. For liquid form preparations, the active compound can be mixed with water or other solvent, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethyl formamide, oils (for example, cottonseed, ground corn, germ, live, caster and sesamine oil), glycerol and fatty acid ester of sorbitan and mixture thereof.

Besides inert diluents, the oral compositions can also include adjuvants, for example, wetting agents, emulsifying agents, suspending agents, sweetening agents, flavoring agents and perfuming agents.

The formulations as described herein may be formulated so as to provide quick, sustained, or delayed release of the active compound after administration to the patient by employing procedures well-known to the art. The term "patient" as used herein refers to a human or non-human mammal, which is the object of treatment, observation or experiment.

The pharmaceutical preparations can be in unit dosage forms, and in such forms, the preparations are subdivided into unit doses containing appropriate quantities of an active compound.

The amount of a compound disclosed herein that will be effective in the treatment of a particular disorder or condition can be determined by standard clinical techniques. In addition, in vitro or in vivo assays may optionally be employed to help identify optimal dosage ranges.

Examples set forth below demonstrate general synthetic procedures for preparation of particular representative compounds. The examples are provided to illustrate particular aspects of the disclosure, and do not constrain the scope of the present invention as defined by the claims.

EXAMPLES

General Procedure

Schemes I and Ib
Step 1: Preparation of β-ketoamide-1 (Formula IV and IVb)

A mixture of β ketoester Formula II, 1 equiv.), amine (Formula III, 1 equiv) 1,2-ethylene diamine (0.01 equiv) in xylene was refluxed with the azeotropic removal of water. After the completion of reaction, solvent was evaporated & the residue purified on column (silica gel; 100-200 mesh). Compounds of Formula IVb can be prepared analogously. The following intermediates were prepared following above general procedure 4-Methyl-3-oxo-pentanoic acid
(3-acetylphenyl)-amide $^1$H NMR (CDCl$_3$): δ 1.19 (d, J=6.9 Hz, 6H), 2.61 (s, 3H), 2.75 (sep, J=6.9 Hz, 1H), 3.64 (s, 2H), 7.43 (t, J=7.8 Hz, 1H), 7.71 (d, J=7.8 Hz, 1H), 7.87 (d, J=8.1 Hz, 1H), 8.08 (s, 1H), 9.44 (brs, 1H); MS (positive ion mode): m/z 248 [M+1]; Yield: 49%

4-Methyl-3-oxo-pentanoic acid
(4-acetylphenyl)-amide $^1$H NMR (CDCl$_3$): δ 1.19 (d, J=6 Hz, 6H), 2.58 (s, 3H), 2.75 (sep, J=6 Hz, 1H), 3.65 (s, 2H), 7.67 (d, J=6 Hz, 2H), 7.95 (d, J=36 Hz, 2H), 9.60 (s, 1H), MS (positive ion mode): m/z 248 [M+1]; Yield 54%

4-Methyl-3-oxo-pentanoic acid
(2,4-dimethylphenyl)-amide $^1$H NMR (CDCl$_3$): δ 1.18 (d, J=6 Hz, 6H), 2.29 (s, 6H), 2.73 (Sep, J=6 Hz, 1H), 3.64 (s, 2H), 7.00 (s, 2H), 7.76 (d, J=6 Hz, 1H), 9.11 (brs, 1H); MS (positive ion mode): m/z 234 [M+1] Yield 72%

4-Methyl-3-oxo-pentanoic acid
4-trifluoromethylbenzyl amide $^1$H NMR (CDCl$_3$): δ 1.14 (d, J=6 Hz, 6H), 2.70 (sept, J=6 Hz, 1H), 3.53 (s, 2H), 4.53 (d, J=6 Hz, 2H), 7.40 (d, J=6 Hz, 2H), 7.59 (d, J=6 Hz, 2H); MS (positive ion mode): m/z 287

4-Methyl-1-piperidin-1-yl-pentane-1,3-dione $^1$H NMR (CDCl$_3$, 300 MHz): δ 1.14 (d, J=6 Hz, 6H), 1.57-1.65 (m, 6H), 2.76 (brs, 1H), 3.20-3.75 (m, 6H);

4-Methyl-3-oxo-pentanoic acid phenylamide

Step 2: Preparation of β-ketoamide-2 (Formula VI and VIb)

To β-ketoamide-1 (Formula IV, 1 equiv) in hexane was added to β-alanine (0.18 equiv), aldehyde (Formula V, 1.1 equiv) and glacial acetic acid (0.16% w/w of β-ketoamide-1). The resulting suspension was heated under reflux with the azeotropic removal of water. The reaction mixture was cooled and product was isolated by filtration. The product was purified by washing the precipitate with hot hexane, water and dried in vacuo to afford β-ketoamide-2. Compounds of Formula VIb can be prepared analogously. The following intermediates were prepared following above general procedure 2-Benzylidine-4-methyl-3-oxo-pentanoic acid
(3-acetylphenyl)-amide; Isomer-1

$^1$H NMR (CDCl$_3$): δ 1.1 (d, J=6.9 Hz, 6H), 2.50-2.70 (m, 4H), 7.28-7.52 (m, 6H), 7.73 (d, J=7.2 Hz, 1H), 7.93 (d, J=8.1 Hz, 1H), 8.19 (d, J=9.9 Hz, 2H), 9.23 (s, 1H); MS (positive ion mode): m/z 336 [M+1]; Yield: 13%

2-Benzylidine-4-methyl-3-oxo-pentanoic acid
(3-acetylphenyl)-amide; Isomer-2

$^1$H NMR (CDCl$_3$): δ 1.24 (d, J=9 Hz, 6H), 2.60 (s, 3H), 3.39 (sep, J=6 Hz, 1H), 7.33-7.98 (m, 11H); MS (positive ion mode): m/z 336 [M+1]; Yield: 32%

2-Benzylidene-4-methyl-3-oxo-pentanoic acid
(4-acetylphenyl)-amide $^1$H NMR (CDCl$_3$): δ 1.23 (d, J=6.6 Hz, 6H), 2.58 (s, 3H), 3.37 (Sep, J=6.6 Hz, 1H), 7.27-7.42 (m, 3H), 7.49-7.73 (m, 5H), 7.95 (d, J=8.7 Hz, 2H); MS (positive ion mode): m/z 336 [M+1]
Yield 48%

2-Benzylidene-4-methyl-3-oxo-pentanoic acid
(2,4-dimethylphenyl)-amide $^1$H NMR (CDCl$_3$): δ 1.23 (d, J=6 Hz, 6H), 1.99 (s, 1H), 2.29 (s, 1H), 3.38 (Sep, J=6 Hz, 1H), 6.97 (s, 1H), 7.04 (d, J=6 Hz, 1H), 7.30 (s, 1H), 7.35-7.45 (m, 3H), 7.53-7.72 (m, 7H)
MS (positive ion mode): m/z 323 [M+1]; Yield 50%

2-Benzylidine-4-methyl-3-oxo-pentanoic acid
4-trifluoromethylbenzyl amide $^1$H NMR (CDCl$_3$, 300 MHz): δ 1.19 (d, J=6.9 Hz, 6H), 3.30 (sept, J=6.9 Hz, 1H), 6.16 (brs, 1H), 7.26-7.60 (m, 10H)

2-Benzylidene-4-methyl-1-piperidin-1-yl-pentane-1,3-dione $^1$H NMR (CDCl$_3$, 300 MHz): δ 0.88-0.97 (m, 2H), 1.15-1.35 (m, 8H), 1.43-1.62 (m, 4H), 3.13-3.30 (m, 3H), 3.61 (brs, 1H), 3.78 (brs, 1H), 7.38 (brs, 3H), 7.54 (brs, 3H); MS (positive ion mode): m/z 286 (M⁺+1)

2-(4-Cyanobenzylidene)-4-methyl-3-oxo-pentanoic acid phenylamide $^1$H NMR (CDCl$_3$): δ 1.23 (d, J=6 Hz, 6H), 3.34 (Sep, J=6 Hz, 1H), 7.18 (t, J=6 Hz, 1H), 7.36 (t, J=6 Hz, 2H), 7.48 (d, J=6 Hz, 2H), 7.57 (s, 1H), 7.65 (s, 4H), 7.81 (s, 1H); MS (positive ion mode): m/z 319 [M+1]; Yield: 67%

Step 3: Preparation of Diketone (Formula VIII and VIIIb)

β-ketoamide-2 (Formula VI, 1 equiv), aldehyde (Formula VII, 1.1 equiv), triethylamine (1 equiv) ethanol and 3-ethyl-5-(2-hydroxyethyl)-4-methyl thiazolium bromide (0.2 equiv) were placed in a vial. The contents were flushed with N$_2$ and the vial was capped immediately and was heated to 78° C. After the completion of reaction, contents were cooled and triturated with ethyl acetate. The organic layer was washed with 6N hydrochloric acid, water, dried over anhydrous sodium sulphate, concentrated on rotary evaporator and residue was purified on a chromatographic column (silica gel, 100-200 mesh). Compounds of Formula VIIIb can be prepared analogously. The following intermediates were prepared following above general procedure

2-[2-(Fluorophenyl)-2-oxo-1-phenyl-ethyl]-4-methyl-3-oxo-pentanoic acid (3-acetylphenyl)-amide $^1$H NMR (CDCl$_3$): δ 1.15 (d, J=6 Hz, 3H), 1.20 (d, J=6 Hz, 3H), 2.58 (s, 3H), 2.99 (sep, J=6 Hz, 1H), 4.61 (d, J=12 Hz, 1H), 5.38 (d, J=12 Hz, 1H), 7.05 (t, J=9 Hz, 2H), 7.15-7.44 (m, 6H), 7.54-7.72 (m, 4H), 7.94-8.05 (m, 2H); MS (positive ion mode): m/z 460 [M+1]; Yield: 55%

2-[2-(4-Fluorophenyl)-2-oxo-1-phenylethyl]-4-methyl-3-oxo-pentanoic acid (4-acetylphenyl)-amide $^1$H NMR (CDCl$_3$): δ 1.16 d, J=6.9 Hz, 3H), 1.23 (d, J=6.9 Hz, 3H), 2.55 (s, 3H), 2.99 (Sep, J=6.6 Hz, 1H), 4.56 (d, J=10.5 Hz, 1H), 5.35 (d, J=10.8 Hz, 1H), 7.04 (t, J=8.7 Hz, 3H), 7.18-7.37 (brm, 6H), 7.48 (s, 1H), 7.86 (d, J=8.4 Hz, 2H), 7.87-8.03 (m, 2H); MS (positive ion mode): m/z 460 [M+1]; Yield 64%

2-[2-(4-Fluorophenyl)-2-oxo-1-phenylethyl]-4-methyl-3-oxo-pentanoic acid (2,4-dimethylphenyl)-amide $^1$H NMR (DMSO-d$_6$): δ 0.99 (d, J=6.6 Hz, 3H), 1.19 (d, J=6.9 Hz, 3H), 1.67 (s, 3H), 2.18 (s, 3H), 3.00 (Sep, J=6.9 Hz, 1H), 4.94 (d, J=11.1 Hz, 1H), 5.36 (d, s=10.8 Hz, 1H), 6.68 (d, J=8.1 Hz, 1H), 6.82-6.93 (m, 2H), 7.17-7.45 (m, 7H), 8.08-8.24 (m, 2H), 9.60 (brs, 1H) MS (positive ion mode): m/z 446 [M+1]; Yield 66%

2-[2-(4-Fluorophenyl)-2-oxo-1-phenyl-ethyl]-4-methyl-3-oxo-pentanoic acid 4-trifluoromethylbenzyl amide $^1$H NMR (CDCl$_3$, 300 MHz): δ 1.10 (d, J=6.6 Hz, 3H), 1.16 (d, J=7.2 Hz, 3H), 2.88 (sept, J=6.9 Hz, 1H0, 4.15 (dd, J=15 & 4.8 Hz, 1H), 4.40 (dd, J=15.9 & 6.6 Hz, 1H), 4.46 (d, J=11.1 Hz, 1H), 5.32 (d, J=10.8 Hz, 1H), 5.80 (brs, 1H), 6.89 (d, J=7.8 Hz, 2H), 6.97 (t, J=8.4 Hz, H), 7.45 (d, J=7.5 Hz, 2H), 7.94-7.98 (m, 2H); MS (positive ion mode): m/z 500 (M⁺+1}

1-(4-Fluorophenyl)-5-methyl-2-pentyl-3-(piperidine-1-carbonyl-hexane-1,4-dione $^1$H NMR (CDCl$_3$, 300 MHz): δ 1.05 (d, J=6.9 Hz, 3H), 1.19 (d, J=7.1 Hz, 4H), 1.45 (brs, 5H), 2.62 (sept, J=6.8 Hz, 1H), 2.95-3.15 (m, 1H), 3.20-3.40 (m, 2H), 3.45-3.60 (m, 1H), 4.99 (d, J=10.5 Hz, 1H), 5.34 (d, J=10.6 Hz, 1H), 7.03 (t, J=8.5 Hz, 2H), 7.24 (brs, 5H), 7.97-8.07 (m, 2H); MS (positive ion mode): m/z 493 (M⁺+1)

2-[1-(4-Cyanophenyl)-2-(4-fluorophenyl)-2-oxo-ethyl]-4-methyl-3-oxo-pentanoic acid phenylamide MS (positive ion mode): m/z 443 [M+1]

Step 4: Preparation of Pyrrole (Formula X and Xb)

A mixture of diketone (Formula VIII, 1 equiv), amine (Formula IX, 1.00, equiv) and pivalic acid (1.03 equiv) in heptane:toluene:tetrahydrofuran (4:1:1) was refluxed and water was removed using Dean Stark trap. After the completion of reaction, solvents were removed and the residue was dissolved in ethyl acetate. The organic layer was washed in saturated sodium bicarbonate, water, dried over anhydrous sodium sulphate, concentrated on rotary evaporator and the residue was purified on a chromatographic column (silica gel, 100-200 mesh). Compounds of Formula Xb can be prepared analogously. The following intermediates were prepared following above general procedure

(6-{2-[3-(3-Acetylphenylcarbamoyl)-5-(4-fluorophenyl)-2-isopropyl-4-phenyl-pyrrol-1-yl]-ethyl}-2,2-dimethyl-[1,3]dioxan-4-yl)-acetic acid tert-butyl ester $^1$H NMR (CDCl$_3$): δ 1.30 (s, 3H), 1.36 (s, 3H), 1.43 (s, 9H), 1.53 (d, J=6 Hz, 6H), 1.67 (brs, 2H), 2.20-2.43 (m, 2H), 2.52 (s, 3H), 3.52-3.75 (m, 2H), 3.76-3.88 (m, 1H), 4.00-4.22 (m, 2H), 6.85-7.05 (m, 3H), 7.10-7.51 (m, 10H), 7.58 (d, J=9 Hz, 1H); MS (positive ion mode): m/z 697 [M+1]; Yield: 23%

(6-{2-[3-(4-Acetylphenylcarbamoyl)-5-(4-fluorophenyl)-2-isopropyl-4-phenyl-pyrol-1-yl]-ethyl}-2,2-dimethyl-[1,3]dioxan-4-yl)-acetic acid tert-butyl ester $^1$H NMR (CDCl$_3$): δ 1.31 (s, 3H), 1.38 (s, 3H), 1.44 (s, 9H), 1.53 (d, J=9 Hz, 6H), 1.66 (brs, 2H), 2.22-2.49 (m, 2H), 2.54 (s, 3H), 3.49-3.75 (m, 2H), 4.00-4.25 (m, 2H), 7.01 (t, J=6 Hz, 2H), 7.06-7.26 (m, 10H), 7.81 (d, J=9 Hz, zH); MS (positive ion mode): m/z 698 [M+1]; Yield: 14%

(6-{2-[3-(2,4-Dimethylphenylcarbamoyl)-5-(4-fluorophenyl)-2-isopropyl-4-phenyl-pyrrol-1-yl]-ethyl}-2,2-dimethyl-[1,3]dioxan-4-yl)-acetic acid tert-butyl ester $^1$H NMR (CDCl$_3$): δ 1.30 (s, 3H), 1.36 (s, 3H), 1.43 (s, 9H), 1.52 (d, s=6 Hz, 6H), 1.65-1.76 (m, 2H), 2.18-2.32 (m, 4H), 2.33-2.47 (m, 1H), 3.48 (Sep, J=6 Hz, 1H), 3.63-3.90 (m, 2H), 4.0-4.25 m, 2H), 6.72 (s, 1H), 6.81 (s, 1H), 6.99 (t, S=6 Hz, 3H), 7.07-7.25 (m, 7H), 7.88 (d, J=6 Hz, 1H); MS (positive ion mode): m/z 684 [M+1]; Yield 21%

(6-{2-[2-(4-Fluorophenyl)-5-isopropyl-3-phenyl-4-(4-trifluoromethylbenzylcarbamoyl)-pyrrol-1-yl]-ethyl}-2,2-dimethyl-[1,3]dioxan-4-yl)acetic acid tert-butyl ester $^1$H NMR (CDCl$_3$, 300 MHz): δ 0.8-1.2 (m, 2H), 1.29 (s, 3H), 1.35 (s, 3H), 1.43 (s, 9H), 1.63 (brs, 2H), 2.22-2.27 (m, 1H), 2.38 (dd, J=15.0 & 6.0 Hz, 1H), 9.36-3.50 (m, 1H), 3.6-3.7 (m, 1H), 3.71-3.85 (m, 1H), 4.1-4.25 (m, 2H), 4.38 (d, J=6.0 Hz, 2H), 7.02-7.16 (m, 12H), 7.41 (d, J=9.0 Hz, 2H); MS (positive ion): m/z 737.4 [M+1]$^+$ 6-{2-[2-(4-Fluorophenyl)-5-isopropyl-3-phenyl-4-(piperidine-1-carbonyl)-pyrrol-1-yl]-ethyl}-2,2-dimethyl-[1,3]dioxan-4-yl)-acetic acid tert-butyl ester $^1$H NMR (CDCl$_3$, 300 MHz): δ 0.99-1.60 (m, 29H), 2.17-2.52 (m, 2H), 2.80-3.25 m, 3H), 3.35-3.50 (m, 1H), 3.65-3.90 (m, 3H), 3.90-4.25 (m, 3H), 6.91-7.19 (m, 9H); MS (positive ion mode): m/z 646 (M$^+$+1)

(6-{2-[3-(4-cyanophenyl)-5-isopropyl-2-(4-fluorophenyl)-4-(phenylamino)carbonyl-pyrrol-1-yl]-ethyl}-2,2-dimethyl-[1,3]dioxan-4-yl)acetic acid tert-butyl ester $^1$H NMR (CDCl$_3$): δ 1.30 (s, 3H), 1.36 (s, 3H), 1.44 (s, 9H), 1.50 (d, J=6.9 Hz, 6H), 1.67 (brs, 3H), 1.55-1.75 (brm, 3H), 2.20-2.40 (m, 2H), 3.38 (sep, J=6.6 Hz, 1H), 3.63-3.88 (m, 2H), 3.97-4.24 (m, 2H), 6.85 (s, 1H), 6.96-7.48 (m, 12H); MS (positive ion mode): m/z 680 [M+1]; Yield: 20%

Step 5: Preparation of Hemi Calcium Salt of Compound of Formula XI and XIb (a) To a solution of a compound of Formula X in methanol and tetrahydrofuran (1:1) was added 1N hydrochloric acid (3 equiv) and the mixture was stirred at ambient temperature. After the complete hydrolysis of the ketal, the reaction mixture was cooled to 0° C. and sodium hydroxide pellets (6 equiv) were added. The reaction was then stirred at ambient temperature. At the end of ester hydrolysis, solvents were removed and the residue was dissolved in water; aqueous layer was washed with ether, and was neutralized with 1N hydrochloric acid. The organic phase was extracted into ethyl acetate, and concentrated. The residue was then purified on a chromatographic column (silica gel 100-200 mesh).

(b) To an aqueous solution of sodium salt of acid (is prepared by adding 1 equivalent 1N sodium hydroxide solution) was added dropwise an aqueous solution (1M) of calcium acetate (0.55 equiv). White precipitate was obtained, which was filtered off, washed with copious amount of water, and dried in vacuo.

Compounds of Formula XIb and XIIb can be formed analogously. The following compounds were prepared following above general procedure Hemi calcium salt of (3R,5R)-7-[2-(4-fluorophenyl)-5-isopropyl-3-phenyl-4-[(3-acetylphenylamino)carbonyl]-pyrrol-1-yl]-3,5-dihydroxy-heptanoic acid $^1$H NMR (DMSO-d$_6$): δ 1.23 (brs, 2H), 1.38 (d, J=6 Hz, 6H), 1.63 (brs, 2H), 1.90-2.15 (m, 2H), 3.52 (brs, 1H), 3.76 (brs, 2H), 3.99 (brs, 1H), 6.95-7.45 (m, 10H), 7.60 (d, J=7.5 Hz, 1H), 7.71 (d, J=7.5 Hz, 1H), 8.15 (s, 1H), 9.98 (s, 1H, D$_2$O exchanged); MS (positive ion mode): m/z 601 [Acid+1]; Yield: 21.35; m.pt: 167.5-204° C.

Hemi calcium salt of (3R,5R)-7-[2-(4-fluorophenyl)-5-isopropyl-3-phenyl-4-[(4-acetylphenylamino)carbonyl]-pyrrol-1-yl]-3,5-dihydroxy-heptanoic acid $^1$H NMR (DMSO-d$_6$): δ 1.24 (brs, 2H), 1.37 (d, J=6 Hz, 6H), 1.58 (brs, 2H), 1.88-1.99 (m, 1H), 2.00-2.12 (m, 1H), 3.53 (brs, 1H), 3.73 (brs, 2H), 3.96 (brs, 1H), 7.09 (brs, 5H), 7.14-7.37 (m, 4H), 7.66 (d, J=9 Hz, 2H), 7.85 (d, J=9 Hz, 2H), 10.21 (s, 1H, D$_2$O exchanged); MS (positive ion mode): m/z 601 [Acid+1]; Yield 23%; m.pt 188.9-216.5° C.

Hemi calcium salt of (3R,5R)-7-[2-(4-fluorophenyl)-5-isopropyl-3-phenyl-4-[(2,4-dimethylphenylamino)carbonyl]-pyrrol-1-yl]-3,5-dihydroxy-heptanoic acid $^1$H NMR (DMSO): δ 1.29 (brs, 2H), 1.31-1.76 (m, 1H), 1.87-2.01 (dd, J=15 & 6 Hz, 1H), 2.02-2.15 (dd, J=15 & 3 Hz, 1H), 2.19 (s, 3H), 3.59 (brs, 1H), 3.76 (brs, 2H), 3.95 (brs, 1H), 6.85-6.95 (m, 2H), 7.05-7.33 (m, 10H), 8.78 (s, 1H, D$_2$O exchanged); MS (positive ion mode): m/z 587 [Acid+1]; Yield 45%; m.p 172.6-198.9° C.

Hemi calcium salt of (3R,5R)-7-[2-(4-fluorophenyl)-5-isopropyl-3-phenyl-4-[(4-trifluoromethylbenzylamino)carbonyl)]-pyrrol-1-yl]-3,5-dihydroxy-heptanoic acid $^1$H NMR (DMSO-d$_6$, 300 MHz): δ 1.15-1.24 (m, 2H), 1.31 (d, J=6 Hz, 6H), 1.48-1.56 (m, 2H), 1.84 (dd, J=1158, 7.8 Hz, 1H), 2.01 (dd, J=15 & 4.2 Hz, 1H), 3.15-3.33 (m, 1H), 3.42 (brs, 1H), 3.50 (brs, 1H), 3.68-3.73 (m, 2H), 3.80-4.02 (m, 1H), 4.29 d, J=5.4 Hz, 1H), 6.99 (brs, 2H), 7.05 (brs, 3H), 7.12-7.23 (m, 6H), 7.50 (d, J=8.1 Hz, 2H), 8.24 (t, J=5.4 Hz, 1H); MS (positive ion mode): m/z 641 (acid+1)

Hemi calcium salt of (3R,5R)-7-[2-(4-fluorophenyl)-5-isopropyl-3-phenyl-4-(piperidine-1-carbonyl)-pyrrol-1-yl]-3,5-dihydroxy-heptanoic acid $^1$H NMR (DMSO-d$_6$, 300 MHz, D$_2$O exchanged): δ 1.08-1.13 (m, 2H), 1.24 (brs, 7H), 1.27 (d, J=9 Hz, 6H), 1.43 (brs, 2H), 2.02 (dd, J=15 & 6 Hz, 1H), 2.15-2.19 (m, 1H), 2.88-2.95 (m, 2H), 3.12-3.24 m, 2H), 3.64-3.69 (m, 3H), 6.95 (d, J=6 Hz, 2H), 7.05-7.15 (m, 5H), 7.25 (brs, 2H), 8.08 (s, 1H).

Hemi calcium salt of (3R,5R)-7-[2-(4-fluorophenyl)-5-isopropyl-3-(4-cyanophenyl)-4-[(phenylamino)carbonyl)]-pyrrol-1-yl]-3,5-dihydroxy-heptanoic acid $^1$H NMR (DMSO-d$_6$): δ 1.24 (brs, 2H), 1.37 (d, J=6 Hz, 6H), 1.45-1.73 (m, 2H), 1.87-2.15 (m, 2H), 3.10-3.60 (m, 2H), 3.70-3.90 (brm, 2H), 3.91-4.08 (brim, 1H), 7.01 (t, J=6 Hz, 1H), 7.13-7.35 (m, 8H), 7.45-7.63 (m, 4H), 10.02 (s, 1H, D$_2$O exchanged); MS (positive ion mode): m/z 584 [Acid+1]; Yield: 87%; m.pt. 197.7-222.1° C.

Scheme Ia

Step 1: Preparation of Compound of Formula XIV

Compound XI (prepared following the appropriate steps of Scheme I to produce a compound of Formula X with appropriate substitution) was dissolved in tetrahydrofuran:methanol (1:2) mixture and 1N lithium hydroxide (equiv) was added. The reaction mixture was stirred at 0° C. for 12 to 15 hours. After completion of reaction, reaction mixture was acidified and the solvent was evaporated under reduced pressure to get crude product. The crude product was purified by column chromatography (silica gel—100-200 mesh) using 50% ethyl acetate in hexane. The following intermediates wee prepared in this fashion.

4-{[1-[2-(6-tert-butoxycarbonylmethyl-2,2-dimethyl-[1,3]dioxan-4-yl)-ethyl]-5-(4-fluorophenyl)-2-isopropyl-4-phenyl-1H-pyrrol-3-carbonyl]-amino}-benzoic acid $^1$H NMR (CDCl$_3$): δ 1.03-1.11 (m, 1H), 1.26 (s, 3H), 1.30 (s, 3H), 1.43 (s, 9H), 1.53 (d, J=7.2 Hz, 3H), 1.65-1.69 (m, 2H), 2.23 (dd, J=15.6 & 6.3 Hz, 1H), 2.40 (dd, J=15.6 & 6.3 Hz, 1H), 3.63-3.71 (m, 2H), 3.75-3.8 (m, 1H), 4.05-4.20 (m, 2H), 6.96-7.20 (m, 12H), 7.90 (d, J=8.4 Hz, 2H); MS (positive ion mode): m/z 698 (M$^+$+1); Yield=51%

Step 2: Preparation of Compound of Formula XV

Method A: Compound XIV (1 equiv) was dissolved in dry tetrahydrofuran and sodium borohydride (2 equiv) was added slowly in two to three fractions. The resulting suspension was stirred for 5 minutes at 0° C. A solution of iodine (1 equiv) in tetrahydrofuran was added slowly at 0° C. and reaction mixture was stirred for 24 to 30 hours at an ambient temperature. At the end of reaction, solvent was evaporated to get crude product. The crude product was purified by column chromatography (silica gel, 100-200 mesh) using 25% ethyl acetate in hexane.

$^1$H NMR (CDCl$_3$, 300 MHz): δ 1.02=1.06 (m, 1H), 1.26 (s, 3H), 1.33 (s, 3H), 1.43 (s, 9H), 1.55 (d, J=6 Hz, 6H), 2.21 (dd, J=15 & 6 Hz, 1H), 2.38 (dd, J=15 & 6 Hz, 1H), 2.40-4.17 (m, 5H), 4.58 (s, 2H), 6.87-7.19 (m, 13H); MS (+ ve ion mode): m/z 685 (M$^+$+1); Yield=87%

Method B: A mixture of compound of Formula XIV (1 equiv.) and tetrahydrofuran (4 mL, Dry) was placed in a 3 neck round bottom flask equipped with a reflux condenser, nitrogen was purged. The reaction mixture was heated at about 50° C. and borane dimethylsulphide (2 equiv.) was added dropwise over 1 hour. Water (6 mL) was added to the reaction mixture, solvent was evaporated. Solid residue was dissolved in ethyl acetate, washed with water and the aqueous layer was extracted with ethyl acetate. The organic layer was washed with brine, dried over anhydrous sodium sulphate, concentrated. The crude product was purified by silica gel column chromatography using ethyl acetate and hexane as eluant.

Yield: 2.16 g (73.72%)

Step 3: Preparation of Hemi Calcium Salt of Formula XVI (a) To a solution of XV in methanol and tetrahydrofuran (1:1) was added 1N hydrochloric acid (3 equiv) and the mixture stirred at an ambient temperature. After the complete hydrolysis of ketal, the reaction-mixture was cooled to 0° C. and sodium hydroxide pellets (6 equiv) were added. The reaction was then allowed to stir at ambient temperature. At the end of ester hydrolysis, solvents were removed and the residue was dissolved in water; the aqueous layer was washed with ether, and neutralized with 1N hydrochloric acid. The organic phase was extracted into ethyl acetate, and concentrated. The residue was then purified on column (silica gel 100-200 mesh).

(b) To an aqueous solution of the sodium salt of the acid (prepared by adding 1 equivalent 1N sodium hydroxide solution) was added dropwise an aqueous solution (1M) of calcium acetate (0.55 equiv). White precipitate was obtained, which was filtered off and washed with copious amount of water, and dried in vacuo.

The following compound was prepared similarly.

Hemi calcium salt of (3R,5R)-7-[2-(4-fluorophenyl)-5-isopropyl-3-phenyl-4-[(4-hydroxymethylphenylamino)carbonyl]-pyrrol-1-yl]-3,5-dihydroxy-heptanoic acid $^1$H NMR (DMSO-d$_6$): δ 1.22-1.62 (M, 11H), 1.98 (dd, J=15 & 8.1 Hz, 1H), 2.06-2.16 (m, 1H), 3.25-3.37 (m, 2H), 3.57 (brs, 2H), 3.80 (brs, 1H), 4.43 (s, 2H), 7.03-7.28 (m, 12H), 7.50 (d, J=6H, 2H), 9.80 (s, 1H); MS (positive ion mode): m/z 589 (Acid+1); Yield=31%; m.p.=189-204° C.

Scheme IIa

Step I: Preparation of Compound of Formula XVa

A compound of Formula XIIIa (1 equiv.) and a mixture of 1N hydrochloric acid:methanol:tetrahydrofuran (2:5:5) were stirred at room temperature for about 7 hours. At the end of reaction, sodium hydroxide pellets (7 equiv.) were added and the reaction mixture was further stirred at room temperature for about 5 hours. Reaction mixture was concentrated and the residue was dissolved in distilled water and acidified to ~1 pH with 1N hydrochloric acid. The aqueous layer was extracted with ethyl acetate, washed with water, brine and dried over anhydrous sodium sulphate. Organic layer was concentrated and adsorbed over silica gel (5% methanol-dichloromethane). The following compound was prepared by following above procedures (3R,5R)-7-[2-(4-fluorophenyl)-5-isopropyl-3-phenyl-4-[4-carboxyphenyl)amino)carbonyl]-pyrrol-1-yl]-3,5-dihydroxy-heptanoic acid Yield: 5 g (84.6%)

Step II: Preparation of Disodium Salt of Compound of Formula XVa

A compound of XVa (1 equiv.), tetrahydrofuran:methanol (1:1) and sodium hydroxide (1N, 2 equiv.) solution were stirred at ambient temperature for about 2 hours. Disodium salt of compound of Formula XVa was isolated by evaporating solvent under reduced pressure. The residue was washed with diethylether, dried in vacuo to afford the pure compound in a yield of 4.5 g (84.9%). The following compound was prepared by following above procedures.

Disodium salt of (3R,5R)-7-[2-(4-fluorophenyl)-5-isopropyl-3-phenyl-4-[4-carboxyphenyl)amino)carbonyl]-pyrrol-1-yl]-3,5-dihydroxy-heptanoic acid $^1$H NMR (DMSO, 300 MHz): δ 1.135-1.179 (m, 2H), 1.365 (d, J=6.3 Hz, 6H), 1.752 (brs, 4H), 1.752-1.779 (m, 1H), 1.950-1.998 (m, 1H), 2.733 (s, 1H), 2.89 (s, 1H), 3.607-3.75 (m, 3H), 3.924-4.004 (m, 2H), 6.99-7.07 (m, 5H), 7.155-7.247 (m, 4H), 7.4 (d, J=6 Hz, 2H), 7.70 (d, J=9 Hz, 2H), 9.827 (s, 1H); MS (positive ion mode): m/z 603.13 (Acid$^+$+1); Yield: 4.5 g (84.9%).

Scheme II

Preparation of Compound of Formula XIX

To a solution of a compound of Formula XVIII (4.5 mmoles; prepared according to procedure as described in Tet. Let., 43:1161 (2002) and J. Org. Chem., 50:438 (1985), in toluene (15 ml) was added a compound of Formula V (4.9 mmoles), piperidine (0.02 ml) and acetic acid (0.054 ml). The mixture was heated at reflux with azeotropic removal of water for about 4 to 6 hours. The reaction mixture was concentrated and the residue was extracted in dichloromethane. The organic layer was washed with 1N hydrochloric acid solution, sodium bicarbonate solution, brine, dried over anhydrous sodium sulphate, and concentrated. The crude product was purified on a chromatographic column (silica gel, 100-200 mesh, 2% EtOAc-hexane).

Preparation of Compound of Formula XX

A compound of Formula XIX (6.49 mmoles), a compound of Formula VII (7.14 mmoles), 3-ethyl-5-(2-hydroxyethyl)-4-methyl thiazolium bromide (1.298 mmoles), triethylamine (6.49 mmoles), and ethanol (0.6 ml) were placed in a 30 ml vial, flushed with argon and the vial sealed properly. The reaction mixture was stirred at 70° C. for about 12 to 15 hours. To the reaction mixture was added ethyl acetate, the mixture was washed with water, 6N hydrochloric acid, again with water and brine, dried over anhydrous sodium sulphate, and concentrated to give crude product. The crude product was purified on a chromatographic column (silica gel 100-200 mesh) using 7% ethyl acetate in hexane.

Preparation of Compound of Formula XXI

To a solution of Formula XX (4.62 mmoles) in heptane:toluene:tetrahydrofuran (4:1:1) was added a compound of Formula IX (6.99 mmoles) and pivalic acid (4.768 mmoles). The mixture was refluxed with azeotropic removal of water for about 22 to 25 hours. The reaction mixture was concentrated, ethyl acetate was added, the reaction mixture was washed with sodium bicarbonate solution and brine, dried over anhydrous sodium sulphate and concentrated to give the crude product. The crude product was purified on column (silica gel, 100-200 mesh) using 7% ethyl acetate in hexane.

Preparation of Compound of Formula XXII

To a solution of a compound of Formula XXI (0.8 g) in methanol:dioxan (2:8) mixture was added 10% palladium carbon (50% wet, 60% w/w). The resulting reaction mixture was hydrogenated at 40 psi for about 2.5 hours. After the reaction was over, the reaction mixture was passed through celite and the resulting solution was concentrated under vacuum to give the required product, which was further used as such for next step.

Preparation of Compound of Formula X: Path a

To a solution of a compound of Formula XXII (1 equiv) in benzene at 0° C. under argon, oxalyl chloride (2.0 equiv) was added dropwise. After the evolution of gas had ceased, the reaction mixture was heated on oil bath at 70° C. for 2 hours. The reaction mixture was evaporated to dryness. The residue was dissolved in benzene (dry) and added at ambient temperature to a solution of amine of formula III (1.1 equiv.) in benzene. The reaction mixture was then heated to 70° C. until completion of reaction. Volatiles were removed in vacuo and the residue was purified on a chromatographic column (silica gel, 100-200 mesh). The following compound was prepared following above general procedure (6-{2-[3-(2-Acetylphenylcarbamoyl)-5-(4-fluorophenyl)-2-isopropyl-4-phenyl-pyrrol-1-yl]-ethyl}-2,2-dimethyl-[1,3]dioxan-4-yl)-acetic acid tert-butyl ester $^1$H NMR (CDCl$_3$, 300 MHz): δ 1.0-1.15 (m, 1H), 1.30 (s, 1H), 1.33 (s, 3H), 1.44 (s, 9H), 1.48 (d, J=6.0 Hz, 6H), 2.23 (dd, J=15.0 & 6.0 Hz, 1H), 2.35-2.5 (m, 4H), 3.35 (sept. J=6.0 Hz, 1H), 3.64-3.89 (m, 2H), 4.0-4.25 (m, 2H), 6.93-7.08 (m, 8H), 7.18-7.22 (m, 2H), 7.50 (d, J=9.0 Hz, 1H), 7.69 (d, J=6.0 Hz, 1H), 8.82 (d, J=9.0 Hz, 1H), 11.02 (brs, 1H); MS (positive ion): m/z 697.500 [M+1]$^+$; Yield=59%

Preparation of Compound of Formula X: Path b

To a solution of a compound of Formula XXII (1.2 mmole) in dimethylformamide (2.5 ml) was added diisopropylethylamine (2.4 mmole) and O-benzotriazol-1-yl-N,N,N',N'-tetramethyl uronium hexafluorophosphate (HBTU) (1.2 mmoles). To the resulting clear solution was then added cyclohexylamine (1.2 mmoles) in dimethylformamide (0.5 ml). The reaction mixture was stirred at 50° C. to 60° C. overnight. To the reaction mixture was added water and the mixture was extracted with dichloromethane, the organic layer was washed with water, brine, dried over anhydrous sodium sulphate and concentrated to get the crude product. The crude product was purified by column chromatography (silica gel, 100-200 mesh) using 10% ethyl acetate in hexane. The following compound was prepared as per this protocol.

(6-{2-[3-Cyclohexylcarbamoyl)-5-(4-fluorophenyl)-2-isopropyl-4-phenyl-pyrrol-1-yl]-ethyl}-2,2-dimethyl-[1,3]dioxan-4-yl)-acetic acid tert-butyl ester $^1$H NMR (CDCl$_3$, 300 MHz): δ 0.7-0.88 (m, 2H), 0.97-1.05 (m, 2H), 1.20-1.30 (ma 4H), 1.30-1.34 (s, 3H), 1.43 (s, 9H), 1.47 (d, J=6.9 Hz, 6H), 1.43-1.48 (m, 2H), 1.63 (brs, 3H), 2.25 (dd, J=15 & 6 Hz, 1H), 2.35 (dd, J=15 & 6.9 Hz, 1H), 3.35 (sept, J=6.9 Hz, 1H), 3.69-3.81 (m, 3H), 3.85-4.15 (m, 1H), 4.15-4.25 (m, 1H), 6.91-6.99 (m, 3H), 7.07-7.15 (m, 6H); MS (positive ion mode): m/z 661 (M$^+$+1)

Preparation of Hemi Calcium Salt of Formula XI (a) To a solution of a compound of Formula X in methanol and tetrahydrofuran (1:1) was added 1N hydrochloric acid (3 equiv) and the mixture stirred at ambient temperature. After the complete hydrolysis of ketal, the reaction mixture was cooled to 0° C. and sodium hydroxide pellets (6 equiv) were added. The reaction was then stirred at ambient temperature. At the end of ester hydrolysis, solvents were removed and the residue was dissolved in water; the aqueous layer was washed with ether, and neutralized with 1N hydrochloric acid. The organic phase was extracted into ethyl acetate, and concentrated. The residue was then purified on a chromatographic column (silica gel 100-200 mesh).

(b) To an aqueous solution of the sodium salt of the acid (prepared by adding 1 equivalent 1N sodium hydroxide solution) was added dropwise an aqueous solution (1M) of calcium acetate (0.55 equiv). White precipitate was obtained, which was filtered, washed with copious amount of water, and dried in vacuo.

The following compounds were prepared following above general procedure

Hemi calcium salt of (3R,5R)-7-[2-(4-fluorophenyl)-5-isopropyl-3-phenyl-4-[(cyclohexylamino)carbonyl)]-pyrrol-1-yl]-3,5-dihydroxy-heptanoic acid $^1$H NMR (DMSO-d$_6$, D$_2$O exchanged, 300 MHz): δ 0.99 (brs, 2H), 1.2-1.35 (m, 5H), 1.35-1.50 (m, 7H), 1.55 (m, 4H), 1.90-2.1 (m, 1H), 2.10-2.20 (m, 1H), 3.17-3.20 (m, 1H), 3.51 (brs, 1H), 3.73 (brs, 1H), 7.02-7.36 (m, 9H); MS (positive ion mode): m/z 565 (acid+1).

Hemi calcium salt of (3R,5R)-7-[2-(4-fluorophenyl)-5-isopropyl-3-phenyl-4-[(2-acetylphenylamino)carbonyl]-pyrrol-1-yl]-3,5-dihydroxy-heptanoic acid $^1$H NMR (DMSO-d$_6$, 300 MHz): δ 1.10-1.25 (m, 2H), 1.39 (d, J=6.0 Hz, 6H), 1.5-1.7 (m, 2H), 1.77 (dd, J=150 & 6.0 Hz, 1H), 1.97 (dd, J=15.0 & 3.0 Hz, 1H), 2.38 (s, 3H), 6.94-7.01 (m, 5H), 7.08-7.20 (m, 3H), 7.29-7.34 (m, 2H), 7.56 (t, J=9.0 Hz, 1H), 7.87 (d, J=6.0 Hz, 1H), 8.58 (d, 9.0 Hz, 1H), 10.98 (s, 1H); MS (positive ion): m/z 601.300 [Acid+1]$^+$; Yield=28%; m. pt: 202.6-208.7° C.

Scheme IIIa

Preparation of Compound of Formula XIX

To a solution of a compound of Formula XVIII (4.5 mmoles; prepared according to procedure as described in *Tet. Let.*, 43:1161 (2002) and *J. Org. Chem.*, 50:438 (1985)) in toluene (15 ml) was added a compound of Formula V (4.9 mmoles), piperidine (0.02 ml) and acetic acid (0.054 ml). The mixture was heated at reflux with azeotropic removal of water for about 4 to 6 hours. The reaction mixture was concentrated and the residue was extracted in dichloromethane. The organic layer was washed with 1N hydrochloric acid solution, sodium bicarbonate solution, brine, dried over anhydrous sodium sulphate, and was concentrated. The crude product was purified on a chromatographic column (silica gel, 100-200 mesh, 2% EtOAc-hexane).

$^1$H NMR (CDCl$_3$, 300 MHz): δ 1.02 (d, J=6.9 Hz, 6H), 2.65 (sept, J=7.2 Hz, 1H), 5.26 (s, 2H), 7.25 (s, 2H), 7.25 (brs, 10H), 7.81 (s, 1H)). isomer 2: $^1$H NMR (CDCl$_3$, 300 MHz): δ 1.02 (d, J=6.9 Hz, 6H), 2.65 (sept, J=6.9 Hz, 1H), 5.27 (s, 2H), 7.36 (brs, 10H), 7.82 (s, 1H). MS (+ve ion mode): m/z 309 (M$^+$+1); Yield: 70%

Preparation of Compound of Formula XX

A compound of Formula XIX (6.49 mmoles), a compound of Formula VII (7.14 mmoles), 3-ethyl-5-(2-hydroxyethyl)-4-methyl thiazolium bromide (1.298 mmoles), triethylamine (6.49 mmoles), and ethanol (0.6 ml) were placed in a 30 ml vial, the reaction was flushed with argon and the vial was sealed properly. The reaction mixture was stirred at 70° C. for about 12 to 15 hours. To the reaction mixture was added ethyl acetate, the mixture was washed with water, 6N hydrochloric acid, again with water and brine, was dried over anhydrous sodium sulphate, and was concentrated to give crude product. The crude product was purified on a chromatographic column (silica gel 100-200 mesh) using 7% ethyl acetate in hexane.

$^1$H NMR (CDCl$_3$, 300 MHz): (1:1 mixture of diastereomers) δ 0.48 (d, J=6.9 Hz, 3H), 0.91 (d, J=6.6 Hz, 3H), 1.07 (d, J=6.6 Hz, 3H), 1.21 (d, J=6.9 Hz, 3H), 2.30 (sept, J=6.6 Hz, 1H), 2.82 (sept, 6.6 Hz, 1H), 4.76 (d, J=14 Hz, 1H), 4.77 (d, J=12.3 Hz, 1H), 5.33 (d, J=11.1 Hz, 1H), 5.35 (d, J=11.1 Hz, 1H), 7.02 (t, J=8.4 Hz, 6H), 7.22-7.29 (m, 8H), 7.75-7.99 (m, 4H); MS (+ve ion mode): m/z 433 (M$^+$+1). Yield: 72%

Preparation of Compound of Formula XXI

To a solution of Formula XX (4.62 mmoles) in heptane:toluene:tetrahydrofuran (4:1:1) was added a compound of Formula IX (6.99 mmoles) and pivalic acid (4.768 mmoles). The mixture was refluxed with azeotropic removal of water for about 22 to 25 hours. The reaction mixture was concentrated, ethyl acetate was added, and the reaction mixture was washed with sodium bicarbonate solution and brine, was dried over anhydrous sodium sulphate and was concentrated to give the crude product. The crude product was purified on column (silica gel, 100-200 mesh) using 7% ethyl acetate in hexane.

$^1$H NMR (CDCl$_3$, 300 MHz): δ 0.99-1.08 (m, 2H), 1.25 (s, 3H), 1.34 (s), 1.43 (s, 9H), 1.96 (d, J=6 Hz, 6H), 1.58-1.63 (m, 2H), 2.21 (dd, J=158.6 Hz, 1H), 2.37 (dd, J=15 & 9 Hz, 1H), 3.51 (sept, J=6 Hz), 3.65 (brs, 1H), 3.75-3.85 (m, 1H), 4.00-4.25 (m, 2H), 5.03 (s, 2H), 6.83-7.25 (m, 14H). MS (+ve ion mode): m/z 670 (M$^+$+1). yield 74%

Preparation of Compound of Formula XXII

To a solution of a compound of Formula XXI (0.8 g) in methanol:dioxan (2:8) mixture was added 10% palladium carbon (50% wet, 60% w/w). The resulting reaction mixture was hydrogenated at 40 psi for about 2.5 hours. After the reaction was over, the reaction mixture was passed through celite and the resulting solution was concentrated under vacuum to give the required product, which was further used as such for next step.

$^1$H NMR (CDCl$_3$, 300 MHz): δ 0.95-1.05 (m, 1H), 1.21-1.28 (m, 1H), 1.28 (s, 3H), 1.34 (s, 3H), 1.43 (s, 9H), 1.47 (d, J=7.1 Hz), 1.59-1.65 (m, 2H), 2.22 (dd, J=15.2 & 6.1 Hz, 1H), 2.35 (dd, J=15.2 & 6.1 Hz, 1H), 3.61-3.66 (m, 2H), 3.67-3.86 (m, 1H), 4.00-4.15 (m, 2H), 6.95 (t, J=9 Hz, 2H), 7.06-7.15 (m, 7H) MS (+ve ion mode): m/z 586 (M$^+$+1) Yield 76%

Preparation of Compound of Formula Xa: Path a

To a solution of a compound of Formula XXII (1 equiv) in benzene at 0° C. under argon, oxalyl chloride (2.0 equiv) is added dropwise. After the evolution of gas ceases, the reaction mixture is heated on oil bath at 70° C. for 2 hours. The reaction mixture is evaporated to dryness. The residue is dissolved in benzene (dry) and is added at ambient temperature to a solution of amine of Formula IIIa (1.1 equiv.) in presence of triethylamine, in benzene. The reaction mixture is then heated to 70° C. until completion of reaction. Volatiles are removed in vacuo and the residue is purified on a chromatographic column (silica gel, 100-200 mesh).

Preparation of Compound of Formula Xa: Path b

To a solution of a compound of Formula XXII (1.2 mmole) in dimethylformamide (2.5 ml) is added diisopropylethylamine (2.4 mmole) and O-benzotriazol-1-yl-N,N,N',N'-tetramethyl uronium hexafluorophosphate (HBTU) (1.2 mmoles). To the resulting clear solution is then added cyclohexylamine (1.2 mmoles) in dimethylformamide (0.5 ml). The reaction mixture is stirred at 50° C. to 60° C. overnight. To the reaction mixture is added water and the mixture is extracted with dichloromethane, the organic layer is washed with water, brine, is dried over anhydrous sodium sulphate and is concentrated to get the crude product. The crude product is purified by column chromatography (silica gel, 100-200 mesh) using 10% ethyl acetate in hexane.

Preparation of Hemi Calcium Salt of Formula XIa (a) To a solution of a compound of Formula Xa in methanol and tetrahydrofuran (1:1) is added 1N hydrochloric acid (3 equiv) and the mixture is stirred at ambient temperature. After the complete hydrolysis of ketal, the reaction mixture is cooled to 0° C. and sodium hydroxide pellets (6 equiv) are added. The reaction is then stirred at ambient temperature. At the end of ester hydrolysis, solvents are removed and the residue is dissolved in water; the aqueous layer is washed with ether, and is neutralized with 1N hydrochloric acid. The organics phase is extracted into ethyl acetate, and concentrated. The residue is then purified on a chromatographic column (silica gel 100-200 mesh).

(b) To an aqueous solution of the sodium salt of the acid (is prepared by adding 1 equivalent 1N sodium hydroxide solution) is added dropwise an aqueous solution (1M) of calcium acetate (0.55 equiv). White precipitate is obtained, which is filtered, is washed with copious amount of water, and is dried in vacuo. The following compounds can be prepared following scheme Ib or IIIa or both.

(3R,5R)-7-[2-(4-fluorophenyl)-5-isopropyl-3-phenyl-4-[4-acetoxymethylphenyl)amino)carbonyl]-pyrrol-1-yl]-3,5-dihydroxy-heptanoic acid (Compound No. 2a) and its hemicalcium salt, (3R,5R)-7-[2-(4-fluorophenyl)-5-isopropyl-3-phenyl-4-[4-phenylthiocarbamoyloxymethylphenyl)amino)carbonyl]-pyrrol-1-yl]-3,5-dihydroxy-heptanoic acid (Compound No. 3a) and its hemicalcium salt, (3R,5R)-7-[2-(4-fluorophenyl)-5-isopropyl-3-phenyl-4-[4-propionyloxymethylphenyl)amino)carbonyl]-pyrrol-1-yl]-3,5-dihydroxy-heptanoic acid (Compound No. 4a) and its hemicalcium salt, (3R,5R)-7-[2-(4-fluorophenyl)-5-isopropyl-3-phenyl-4-[4-octylcarbamoyloxymethyl phenyl)amino)carbonyl]-pyrrol-1-yl]-3,5-dihydroxy-heptanoic acid (Compound No. 5a) and its hemicalcium salt, (3R,5R)-7-[2-(4-fluorophenyl)-5-isopropyl-3-phenyl-4-[4-phenylacetoxymethyl phenyl)amino)carbonyl]-pyrrol-1-yl]-3,5-dihydroxy-heptanoic acid (Compound No. 6a) and its hemicalcium salt, (3R,5R)-7-[2-(4-fluorophenyl)-5-isopropyl-3-phenyl-4-[4-phenylcarbamoyloxymethyl phenyl)amino)carbonyl]-pyrrol-1-yl]-3,5-dihydroxy-heptanoic acid (Compound No. 7a) and its hemicalcium salt, (3R,5R)-7-[2-(4-fluorophenyl)-5-isopropyl-3-phenyl-4-[4-benzoyloxymethyl phenyl)amino)carbonyl]-pyrrol-1-yl]-3,5-dihydroxy-heptanoic acid (Compound No. 8a) and its hemicalcium salt, (3R,5R)-7-[2-(4-fluorophenyl)-5-isopropyl-3-phenyl-4-[4-isonicotinoyloxymethyl phenyl)amino)carbonyl]-pyrrol-1-yl]-3,5-dihydroxy-heptanoic acid (Compound No. 9a) and its hemicalcium salt, (3R,5R)-7-[2-(4-fluorophenyl)-5-isopropyl-3-phenyl-4-[4-pyridin-4-ylcarbamoyloxymethyl phenyl)amino)carbonyl]-pyrrol-1-yl]-3,5-dihydroxy-heptanoic acid (Compound No. 10a) and its hemicalcium salt, (3R,5R)-7-[2-(4-fluorophenyl)-5-isopropyl-3-phenyl-4-[4-phenylcarbamoyl phenyl)amino)carbonyl]-pyrrol-1-yl]-3,5-dihydroxy-heptanoic acid (Compound No. 11a) and its hemicalcium salt, (3R,5R)-7-[2-(4-fluorophenyl)-5-isopropyl-3-phenyl-4-[4-cyclohexylcarbamoyl-phenyl)amino)carbonyl]-pyrrol-1-yl]-3,5-dihydroxy-heptanoic acid (Compound No. 12a) and its hemicalcium salt, (3R,5R)-7-[2-(4-fluorophenyl)-5-isopropyl-3-phenyl-4-[4-methylcarbamoyl)-phenyl)amino)carbonyl]-pyrrol-1-yl]-3,5-dihydroxy-heptanoic acid (Compound No. 13a) and its hemicalcium salt, (3R,5R)-7-[2-(4-fluorophenyl)-5-isopropyl-3-phenyl-4-[4-benzylcarbamoyl)-phenyl)amino)carbonyl]-pyrrol-1-yl]-3,5-dihydroxy-heptanoic acid (Compound No. 14a) and its hemicalcium salt, (3R,5R)-7-[2-(4-fluorophenyl)-5-isopropyl-3-phenyl-4-[4-(morpholine-4-carbonyl)-phenyl)amino)carbonyl]-pyrrol-1-yl]-3,5-dihydroxy-heptanoic acid (Compound No. 15) and its hemicalcium salt, (3R,5R)-7-[2-(4-fluorophenyl)-5-isopropyl-3-phenyl-4-[4-(piperidine-1-carbonyl)-phenyl)amino)carbonyl]-pyrrol-1-yl]-3,5-dihydroxy-heptanoic acid (Compound No. 16) and its hemicalcium salt, (3R,5R)-7-[2-(4-fluorophenyl)-5-isopropyl-3-phenyl-4-[4-benzylamino phenyl)amino)carbonyl]-pyrrol-1-yl]-3,5-dihydroxy-heptanoic acid (Compound No. 17) and its hemicalcium salt, (3R,5R)-7-[2-(4-fluorophenyl)-5-isopropyl-3-phenyl-4-[4-(1-hydroxyethyl)phenylamino)carbonyl]-pyrrol-1-yl]-3,5-dihydroxy-heptanoic acid (Compound No. 18) and its hemicalcium salt, (3R,5R)-7-[2-(4-fluorophenyl)-5-isopropyl-3-phenyl-4-[4-(2-hydroxyethyl)phenylamino) carbonyl]-pyrrol-1-yl]-3,5-dihydroxy-heptanoic acid (Compound No. 19) and its hemicalcium salt, (3R,5R)-7-[2-(4-fluorophenyl)-5-isopropyl-3-phenyl-4-[4-(3-hydroxypropyl phenylamino)carbonyl]-pyrrol-1-yl]-3,5-dihydroxy-heptanoic acid (Compound No. 20) and its hemicalcium salt, (3R,5R)-7-[2-(4-fluorophenyl)-5-isopropyl-3-phenyl-4-[(4-methoxymethyl phenylamino)carbonyl]-pyrrol-1-yl]-3,5-dihydroxy-heptanoic acid (Compound No. 21) and its hemicalcium salt, (3R,5R)-7-[2-(4-fluorophenyl)-5-isopropyl-3-phenyl-4-[(4-ethoxymethyl phenylamino)carbonyl]-pyrrol-1-yl]-3,5-dihydroxy-heptanoic acid (Compound No. 22) and its hemicalcium salt, (3R,5R)-7-[2-(4-fluorophenyl)-5-isopropyl-3-phenyl-4-[(4-isopropoxymethyl phenylamino)carbonyl]-pyrrol-1-yl]-3,5-dihydroxy-heptanoic acid (Compound No. 23) and its hemicalcium salt, (3R,5R)-7-[2-(4-fluorophenyl)-5-isopropyl-3-phenyl-4-[(4-propoxymethyl phenylamino)carbonyl]-pyrrol-1-yl]-3,5-dihydroxy-heptanoic acid (Compound No. 24) and its hemicalcium salt, (3R,5R)-7-[2-(4-fluorophenyl)-5-isopropyl-3-phenyl-4-[(4-methoxymethoxymethylphenylamino)carbonyl]-pyrrol-1-yl]-3,5-dihydroxy-heptanoic acid (Compound No. 25) and its hemicalcium salt, (3R,5R)-7-[2-(4-fluorophenyl)-5-isopropyl-3-phenyl-4-[(4-cyclohexyloxymethyl phenylamino)carbonyl]-pyrrol-1-yl]-3,5-dihydroxy-heptanoic acid (Compound No. 26) and its hemicalcium salt, (3R,5R)-7-[2-(4-fluorophenyl)-5-isopropyl-3-phenyl-4-[(4-cyclopentyloxymethyl phenylamino)carbonyl]-pyrrol-1-yl]-3,5-dihydroxy-heptanoic acid (Compound No. 27) and its hemicalcium salt, (3R,5R)-7-[2-(4-fluorophenyl)-5-isopropyl-3-phenyl-4-[(4-benzyloxymethyl phenylamino)carbonyl]-pyrrol-1-yl]-3,5-dihydroxy-heptanoic acid (Compound No. 28) and its hemicalcium salt, (3R,5R)-7-[2-(4-fluorophenyl)-5-isopropyl-3-phenyl-4-[(4-chlorobenzyloxymethyl phenylamino)carbonyl]-pyrrol-1-yl]-3,5-dihydroxy-heptanoic acid (Compound No. 29) and its hemicalcium salt, (3R,5R)-7-[2-(4-fluorophenyl)-5-isopropyl-3-phenyl-4-[(4-methoxybenzyloxymethyl phenylamino)carbonyl]-pyrrol-1-yl]-3,5-dihydroxy heptanoic acid (Compound No. 30) and its hemicalcium salt, (3R,5R)-7-[2-(4-fluorophenyl)-5-isopropyl-3-phenyl-4-[(4-phenoxymethylphenylamino)carbonyl]-pyrrol-1-yl]-3,5-dihydroxy-heptanoic acid (Compound No. 31) and its hemicalcium salt, (3R,5R)-7-[2-(4-fluorophenyl)-5-isopropyl-3-phenyl-4-[(4-chlorophenoxymethyl phenylamino)carbonyl]-pyrrol-1-yl]-3,5-dihydroxy-heptanoic acid (Compound No. 32) and its hemicalcium salt, (3R,5R)-7-[2-(4-fluorophenyl)-5-isopropyl-3-phenyl-4-[(4-acetylaminophenylamino)carbonyl]-pyrrol-1-yl]-3,5-dihydroxy-heptanoic acid (Compound No. 33) and its hemicalcium salt, (3R,5R)-7-[2-(4-fluorophenyl)-5-isopropyl-3-phenyl-4-[(4-benzoylamino phenylamino)carbonyl]-pyrrol-1-yl]-3,5-dihydroxy-heptanoic acid (Compound No. 34) and its hemicalcium salt, (3R,5R)-7-[2-(4-fluorophenyl)-5-isopropyl-3-phenyl-4-[(4-benzenesulfonylamino phenylamino)carbonyl]-pyrrol-1-yl]-3,5-dihydroxy-heptanoic acid (Compound No. 36) and its hemicalcium salt, (3R,5R)-7-[2-(4-fluorophenyl)-5-isopropyl-3-phenyl-4-[4-(3-phenyl-ureido)-phenylamino)carbonyl]-pyrrol-1-yl]-3,5-dihydroxy-heptanoic acid (Compound No. 37) and its hemicalcium salt, (3R,5R)-7-[2-(4-fluorophenyl)-5-isopropyl-3-phenyl-4-[4-(3-methyl-ureido)-phenylamino)carbonyl]-pyrrol-1-yl]-3,5-dihydroxy-heptanoic acid (Compound No. 38) and its hemicalcium salt, (3R,5R)-7-[2-(4-fluorophenyl)-5-isopropyl-3-phenyl-4-[4-(3-benzyl-ureido)-phenylamino)carbonyl]-pyrrol-1-yl]-3,5-dihydroxy-heptanoic acid (Compound No. 39) and its hemicalcium salt, (3R,5R)-7-[2-(4-fluorophenyl)-5-isopropyl-3-phenyl-4-[4-(3-benzyl-thioureido)-phenylamino)carbonyl]-pyrrol-1-yl]-3,5-dihydroxy-heptanoic acid (Compound No. 40) and its hemicalcium salt, (3R,5R)-7-[2-(4-fluorophenyl)-5-isopropyl-3-phenyl-4-[4-(3-phenyl-thioureido)-phenylamino)carbonyl]-pyrrol-1-yl]-3,5-dihydroxy-heptanoic acid (Compound No. 41) and its hemicalcium salt, (3R,5R)-7-[2-(4-fluorophenyl)-5-isopropyl-3-phenyl-4-[4-(3-methyl-thioureido)-phenylamino)carbonyl]-pyrrol-1-yl]-3,5-dihydroxy-heptanoic acid (Compound No. 42) and its hemicalcium salt.

Pharmacological Activity

The compounds disclosed herein have activity as inhibitors of 3-hydroxy-3-methyl-glutamyl coenzyme A (HMG-CoA) reductase, and thus are useful in inhibiting cholesterol biosynthesis and/or in lowering triglycerides.

The compounds described herein are screened in an in-vitro HMG-CoA reductase enzyme assay as described by Kubo et al., *Endocrinology* 120:214 (1987) and Hellar et al., *Biochem and Biophys. Res. Comm.* 50:859 (1973).

HMG-CoA reductase is a rate-limiting enzyme in the cholesterol biosynthesis, catalyzing the following reaction. $[^{14}C]$ HMG-CoA+2NADPH+2H$^+$→$[^{14}C]$ mevanolate+CoA+2NADP$^+$ microsomes, utilizing 2.5 µM $[^{14}C]$ HMG-CoA as a substrate. The reaction is carried out in presence of 100 mM KH$_2$PO$_4$, 20 mM G-6-P, 2.5 mM NADP, 10 mM EDTA, 5 mM DTT and 1.4 G-6-P dehydrogenase, at 37° C. for 15 minutes and quantitating $[^{14}C]$ mevalonate as an end product. For IC$_{50}$ determination, the compounds dissolved in 1% dimethylsulfoxide are preincubated with liver microsomes at 37° C. for 30 minutes.

The IC$_{50}$ for HMG-CoA reductase inhibition in rat liver microsome ranged from 0.1 to 0.96 nM. The compounds disclosed herein ranged from being equipotent to 4 fold more potent than atorvastatin. Some of the compounds disclosed herein were potent than atorvastatin in inhibiting cholesterol synthesis in vivo rat model. Some of the compounds disclosed herein have intrinsic clearance in human liver microsome significantly less than atorvastatin and are not major substrate for CYP3A4 (cytochrome p450 3A4). Some of the compounds exhibit potency and selectivity greater than atorvastatin in inhibition of cholesterol synthesis in rat primary hepatocytes over inhibition of cholesterol synthesis in extra hepatic cells/cell lines [e.g. NRK-49F (Fibroblast) and L6 (Myoblast)].

While the present invention has been described in terms of its specific embodiments, certain modifications and equivalents will be apparent to those skilled in the art and are intended to be included within the scope of the present invention.

We claim:

1. A compound of the structure of Formula I,

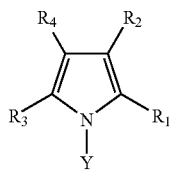

Formula I or a pharmaceutically acceptable salt thereof, pharmaceutically acceptable tautomer, racemate, pure enantiomer, diastereoisomer or a lactone form or N-oxide thereof, wherein

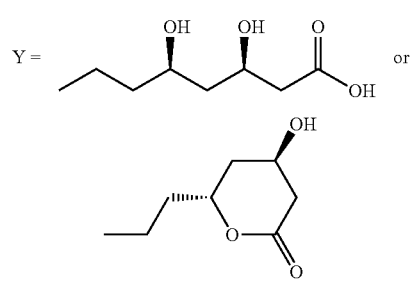

$R_1$ is $C_1$-$C_6$ alkyl, $C_3$-$C_6$ cycloalkyl, or optionally substituted phenyl (wherein up to three substituents are independently selected from halogens, $C_1$-$C_6$ alkyl, cyano, and $C_1$-$C_3$ perfluoroalkyl);

$R_2$ is optionally substituted phenyl (wherein up to three substituents are independently selected from cyano, acetyl, and optionally substituted amino, wherein up to two amino substituents are independently selected from $C_1$-$C_6$ alkyl, $C_3$-$C_6$ cycloalkyl, acetyl, and sulfonamide);

$R_3$ is optionally substituted $C_1$-$C_6$ alkyl or $C_3$-$C_6$ cycloalkyl (wherein substituents are independently selected from halogens, hydroxyl, $C_1$-$C_3$ alkoxy and protected hydroxyl); or $R_3$ is —NR$_8$R$_9$, wherein R$_8$ and R$_9$ are optionally substituted $C_1$-$C_6$ alkyl (wherein the optional substituent(s) is/are selected from halogens, hydroxy, $C_1$-$C_3$ alkoxy and protected hydroxyl);

$R_4$ is

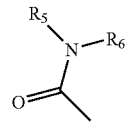

wherein $R_5$ is hydrogen and $R_6$ is aryl substituted with $C_1$-$C_6$ alkyl substituted with one or two substituents independently selected from hydroxyl and protected hydroxyl with the provisio that $R_2$ is phenyl only when:

$R_5$ or $R_6$ is phenyl substituted with hydroxyalkyl.

2. A compound according to claim 1 wherein $R_2$ is phenyl, $R_5$ and $R_6$ are respectively, hydrogen and phenyl substituted with one or more alkyl of from one to six carbon atoms, substituted with hydroxyl.

3. A compound according to claim 1 wherein $R_6$ is phenyl substituted with $C_1$-$C_6$ alkyl substituted with one or two substituents independently selected from hydroxyl and protected hydroxyl.

4. A compound according to claim 1 wherein $R_2$ is phenyl, $R_5$ is hydrogen and $R_6$ is phenyl substituted with hydroxylated alkyl of from one to six carbon atoms.

5. A compound according to claim 1 wherein $R_6$ is 4-hydroxymethyl phenyl.

6. A compound according to claim 1 wherein $R_3$ is alkyl of from one to six carbon atoms or cycloalkyl of from three to six carbon atoms.

7. A compound according to claim 1 wherein $R_3$ is isopropyl.

8. A compound of the chemical formula:

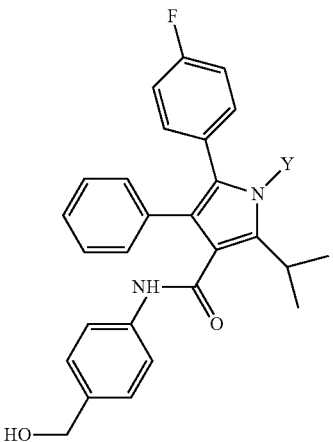

wherein wherein Y = 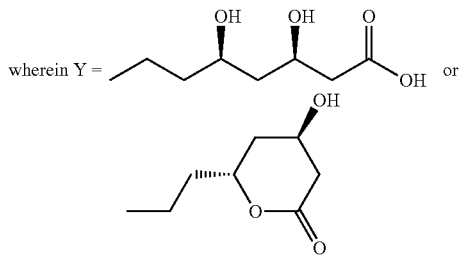

or a pharmaceutically acceptable salt thereof.

9. A compound, which is (3R,5R)-7-[2-(4-fluorophenyl)-5-isopropyl-3-phenyl-4-[(4-hydroxymethylphenylamino)carbonyl]-pyrrol-1-yl]-3,5-dihydroxy-heptanoic acid or a pharmaceutically acceptable salt thereof.

10. A pharmaceutically acceptable salt of a compound of claim 1, wherein the salt is selected from the group consisting of lithium, sodium, potassium, calcium, magnesium, zinc, aluminium, amino acid, ammonium, mono-alkyl ammonium, dialkyl ammonium, trialkyl ammonium and N-methyl glucamine.

11. The pharmaceutically acceptable salt of claim 10, wherein the salt is sodium salt.

12. The pharmaceutically acceptable salt of claim 10, wherein the salt is potassium salt.

13. The pharmaceutically acceptable salt of claim 10, wherein the salt is hemicalcium salt.

14. The pharmaceutically acceptable salt of claim 10, wherein the salt is hemimagnesium salt.

15. The pharmaceutically acceptable salt of claim 10, wherein the salt is hemizinc salt.

16. The pharmaceutically acceptable salt of claim 10, wherein the salt is N-methyl glucamine salt.

17. A pharmaceutical composition comprising a therapeutically effective amount of a compound of claim 10 together with a pharmaceutically acceptable carrier, excipient or diluent.

18. A method of treating diabetes or a disease selected from the group consisting of arteriosclerosis, atherosclerosis, hyperlipidemia, hyperlipoproteinemia, hypercholesterolemia, hypertriglyceridemia, hypertension, stroke, ischemia, peripheral vascular disease, peripheral arterial disease, coronary heart disease, myocardial infarction, cerebral infarction, myocardial microvascular disease, dementia, Alzheimer's disease, angina and restenosis, in a mammal in need of such treatment comprising administering a therapeutically-effective amount of a compound of claim 1 to the mammal.

19. The method according to claim 18 wherein the disease is hyperlipidemia.

20. The method according to claim 18 wherein the disease is hypercholesterolemia.

21. The method according to claim 18 wherein the disease is hyperlipoproteinemia.

22. The method according to claim 18 wherein the disease is hypertriglyceridemia.

23. The method according to claim 18 wherein the disease is hypertension.

* * * * *